United States Patent
Aran Perramon et al.

(10) Patent No.: US 10,577,659 B2
(45) Date of Patent: Mar. 3, 2020

(54) PREDICTIVE METHODS OF ATHEROSCLEROSIS AND STENOSIS

(71) Applicants: INSTITUT D'INVESTIGACIÓ BIOMÈDICA DE BELLVITGE (IDIBELL), Hospitalet de Llobregat-Barcelona (ES); FUNDACIÓ ASSISTENCIAL DE MÚTUA DE TERRASSA, FPC, Terrassa-Barcelona (ES)

(72) Inventors: Josep M. Aran Perramon, Mollet del Valles (ES); Ana Luque Gómez, Barcelona (ES); Jerzy Krupinski, Moiá (ES)

(73) Assignees: INSTITUT D'INVESTIGACIÓ BIOMÈDICA DE BELLVITGE (IDIBELL, Barcelona (ES); FUNDACIÚ ASSISTENCIAL DE MÚTUA DE TERRASSA, FPC, Barcelona (ES)

( * ) Notice: Subject to any disclaimer, the term of this patent is extended or adjusted under 35 U.S.C. 154(b) by 0 days.

(21) Appl. No.: 16/071,949

(22) PCT Filed: Jan. 23, 2017

(86) PCT No.: PCT/EP2017/051316
§ 371 (c)(1),
(2) Date: Jul. 23, 2018

(87) PCT Pub. No.: WO2017/125604
PCT Pub. Date: Jul. 27, 2017

(65) Prior Publication Data
US 2019/0032138 A1 Jan. 31, 2019

(30) Foreign Application Priority Data
Jan. 21, 2016 (EP) .................................. 16382025

(51) Int. Cl.
| | | |
|---|---|---|
| A61K 48/00 | (2006.01) | |
| C07H 21/02 | (2006.01) | |
| C07H 21/04 | (2006.01) | |
| C12Q 1/6883 | (2018.01) | |
| G01N 33/68 | (2006.01) | |
| C12Q 1/686 | (2018.01) | |

(52) U.S. Cl.
CPC ....... *C12Q 1/6883* (2013.01); *G01N 33/6893* (2013.01); *C12Q 1/686* (2013.01); *C12Q 2600/106* (2013.01); *C12Q 2600/112* (2013.01); *C12Q 2600/178* (2013.01); *G01N 2800/323* (2013.01); *G01N 2800/52* (2013.01)

(58) Field of Classification Search
CPC ........................... A61K 31/713; C12N 15/113
See application file for complete search history.

(56) References Cited

U.S. PATENT DOCUMENTS

2011/0144914 A1 6/2011 Harrington et al.
2012/0196293 A1 8/2012 Juo et al.

FOREIGN PATENT DOCUMENTS

EP           2510116 A2    10/2012
WO      2011072177 A2     6/2011

OTHER PUBLICATIONS

Agarwal et al., "Predicting Effective MicroRNA Target Sites in Mammalian mRNAs", eLife, 2015, 38 pages, vol. 4.
Ambros et al., "A Uniform System for MicroRNA Annotation", RNA, 2003, pp. 277-279, vol. 9.
Andreou et al., "MiRNAs in Atherosclerotic Plaque Initiation, Progression, and Rupture," Trends in Molecular Medicine, 2015, pp. 307-318, vol. 21, No. 5.
Bandyopadhyay et al., "TargetMiner: MicroRNA Target Prediction with Systematic Identification of Tissue-Specific Negative Examples", Bioinformatics, 2009, pp. 2625-2634, vol. 25, No. 9.
Betel et al., "Comprehensive Modeling of MicroRNA Targets Predicts Functional Non-Conserved and Non-Canonical Sites", Genome Biology, 2010, 14 pages, vol. 11, Issue 8.
Chou et al., "MiRTarBase Update 2018: A Resource for Experimentally Validated MicroRNA-target Interactions", Nucleic Acids Research, 2018, D296-D302, vol. 46.
Cipollone et al., "A Unique MicroRNA Signature Associated with Plaque Instability in Humans", Stroke, 2011, pp. 2556-2563, vol. 42, No. 42.
Conroy et al., "Estimation of Ten-Year Risk of Fatal Cardiovascular Disease in Europe: The SCORE Project", European Heart Journal, 2003, pp. 987-1003, vol. 24.
Dweep et al., "MiRWalk-Database: Prediction of Possible MiRNA Binding Sites by "Walking" the Genes of Three Genomes", Journal of Biomedical Informatics, 2011, pp. 839-847, vol. 44.
Dweep et al., "MiRWalk2.0: A Comprenhensive Atlas of MicroRNA-Target Interactions", Nature Methods, 2015, pp. 697, vol. 12, Issue 8.
Friedman et al., "Most Mammalian mRNAs are Conserved Targets of MicroRNAs", Genome Research, 2009, pp. 92-105, vol. 19.
Garcia et al., "Weak Seed-Pairing Stability and High Target-Site Abundance Decrease the Proficiency of Isy-6 and Other MiRNAs", Nat Struct Mol Biol., 2011, pp. 1139-1146, vol. 18, Issue 10.
Grimson et al., "MicroRNA Targeting Specificity in Mammals: Determinants Beyond Seed Pairing", Molecular Cell, 2007, pp. 91-105, vol. 27, Issue 1.
Lewis et al., "Conserved Seed Pairing, Often Flanked by Adenosines, Indiciates that Thousands of Human Genes are MicroRNA Targets", Cell, 2005, pp. 15-20, vol. 120.
Li et al., "Identication of Circulating MicroRNAs as Potential Biomarkers for Detecting Acute Ischemic Stroke", Cell Mol Neurobiol, 2014, pp. 433-447, vol. 35, No. 3.

(Continued)

*Primary Examiner* — Amy H Bowman
(74) *Attorney, Agent, or Firm* — Thompson Coburn LLP; William A. Holtz

(57) ABSTRACT

The present invention relates to methods for diagnosing unstable atherosclerotic plaque, determining the probability of suffering from stroke, selecting a therapy for a subject suffering from carotid artery disease and predicting the progression of atherosclerotic disease.

12 Claims, 7 Drawing Sheets

(56) References Cited

OTHER PUBLICATIONS

Maragkakis et al., "DIANA—MicroT Web Server Upgrade Supports Fly and Worm MiRNA Target Prediction and Bibliographic MiRNA to Disease Association", Nucelic Acids Research, 2011, pp. W145-W148, vol. 39.

Paraskevopoulou et al., "DIANA—MicroT Web Server v5.0: Service Integration into MiRNA Functional Analysis Workflows", Nucleic Acids Research, 2013, pp. W169-W173, vol. 41.

Reczko et al., "Functional MicroRNA Targets in Protein Coding Sequences", Bioinformatics, 2012, pp. 771-776, vol. 28, No. 6.

Tan et al., "Expression Profile of MircoRNAs in Young Stroke Patients", Plos One, 2009, 9 pages, vol. 4, Issue 11.

Wang, "Improving MicroRNA Target Prediction by Modeling with UnAmbiguously Identifed MicroRNA-Target Pairs CLIP—Ligation Studies", Bioinformatics, 2016, pp. 1316-1322, vol. 32, Issue 9.

Wong et al., "Mi-RDB: An Online Resource for MicroRNA Target Prediction and Functional Annotations", Nucleic Acids Research, 2015, pp. D146-D152, vol. 43.

D

E

F

D

E

F

PREDICTIVE METHODS OF ATHEROSCLEROSIS AND STENOSIS

FIELD OF THE INVENTION

The present invention is related to the technical field of diagnostics and therapeutics, particularly to methods for diagnosing unstable atherosclerotic plaque, determining the probability of suffering from stroke, selecting a therapy for a subject suffering from carotid artery disease and predicting the progression of atherosclerotic disease.

BACKGROUND OF THE INVENTION

Stroke is responsible for more than 10% of deaths worldwide and represents one of the leading causes of disability in the developed countries. Low-degree, chronic inflammation due to the present lifestyle (diet, stress, sedentariness) have a negative impact in the vascular homeostasis and, consequently, its main outcomes (obesity, hypertension, high blood cholesterol, cigarette smoking, diabetes) have become undisputed primary risk factors for the occurrence of stroke. Indeed, atherosclerosis, the main vascular vessel pathology, results from the inflammatory build-up of lipid-laden macrophages in the vessel wall, although its precise molecular pathogenic mechanism is still poorly understood. Carotid artery atherosclerosis has become the major high risk mechanism for the occurrence of ischemic stroke, which represents more than 80% of all cerebrovascular events. Preventive measures have been developed to avoid carotid stenosis, such as surgical plaque removal by carotid endarterectomy (CEA) or endovascular stent placement (CAS), whose benefit has been suggested in several clinical trials. Nevertheless, the surgical management of asymptomatic patients with >70% carotid estenosis and <10 years of life expectancy is presently highly controversial due to the improvement of the medical treatment.

Methods for assessing the cardiovascular health of a subject comprising determination of the expression levels of particular miRNA markers (miR-378, miR-497, miR-21, miR-15b, miR-99a, miR-29a, miR-24, miR-30b, miR-29c, miR-331.3p, miR-19a, miR-22, miR-126, let-7b, miR-502.3, and miR-652) have been described in EP2510116 A2. Methods for atherosclerosis diagnosis in a subject based on expression levels of particular miRNA (miR-21, miR221) have been described in US2012196293 A1. A miRNA profiling of patients suffering from ischemic stroke has been performed by Tan et al. (Kay Sin Tan et al. 2009 Plos One 4(11): e7689). Expression of 5 miRNA (miR-125b-2*, -27a*, -422a, -488 and -627) has been shown to be consistently altered in acute stroke irrespective of age or severity or confounding metabolic complications.

The degree of carotid artery stenosis and plaque neovascularization, evaluated through imaging techniques such as contrast-enhanced ultrasound, positron emission tomography/computed tomography (PET/TC), and magnetic resonance, is being considered a most important predictor of carotid plaque vulnerability and, consequently, of increased risk of stroke in patients with carotid artery disease. However, most of the above advanced imaging techniques have not entered routine clinical practice because of its elevated costs. Additionally, a major limitation of these imaging techniques is their application only in advanced stages of atherosclerotic disease, because of its vessel wall anatomy/morphology-based predictive nature.

Thus, novel diagnostic markers using minimally invasive approaches are needed for a more specific and sensitive prediction of atherosclerosis load and progression, and particularly, to reliably identify patients with high-risk carotid plaques for early and accurate stroke risk stratification.

SUMMARY OF THE INVENTION

The authors of the present invention have identified cell-free circulating miRNA miR-638 as a biomarker for vulnerable atherosclerotic plaque identification in patients with high-grade carotid artery stenosis and, consequently, as a prediction biomarker for primary and secondary ischemic stroke risk, particularly in high cardiovascular risk individuals. Accordingly, circulating miRNA miR-638 is also a prognostic biomarker to monitor the effectiveness of a medical treatment.

Therefore, the invention relates in a first aspect to a method for diagnosing unstable atherosclerotic plaque in a subject that comprises
(i) Determining the expression level of circulating miRNA miR-638 in a sample from said subject, and
(ii) Comparing the expression level obtained in (i) to a reference value,
wherein if the expression level of circulating miR-638 in (i) is decreased with respect to the reference value, then the subject is diagnosed with unstable atherosclerotic plaque, or wherein if the expression level of circulating miR-638 in (i) is equal or increased with respect to the reference value, then the subject is not diagnosed with unstable atherosclerotic plaque.

In a second aspect, the present invention relates to a method for determining the probability that a subject suffers from a stroke that comprises
(i) Determining the expression level of circulating miRNA miR-638 in a sample from said subject, and
(ii) Comparing the expression level obtained in (i) to a reference value,
wherein if the expression level of circulating miR-638 in (i) is decreased with respect to the reference value, then the subject shows a high probability of suffering from a stroke, or wherein if the expression level of circulating miR-638 in (i) is equal or increased with respect to the reference value, then the subject shows a low probability of suffering from a stroke.

In a further aspect, the invention relates to a method for the selection of a therapy for a subject suffering from carotid artery disease that comprises
(i) Determining the expression level of circulating miRNA miR-638 in a sample from said subject, and
(ii) Comparing the expression level obtained in (i) to a reference value,
wherein if the expression level of circulating miR-638 in (i) is decreased with respect to the reference value, then a therapy comprising a pharmacological treatment or a revascularization procedure is selected.

In a last aspect, the invention relates to a method for predicting the progression of atherosclerotic disease in a subject known to have suffered from said disease and who has undergone a revascularization procedure, wherein the method comprises
(i) Determining the expression level of circulating miRNA miR-638 in a sample from said subject, and
(ii) Comparing the expression level obtained in (i) to a reference value,
wherein if the expression level of miR-638 in (i) is increased with respect to a reference value, then the atherosclerotic disease will show a slow progression, or wherein if the expression level of miR-638 in (i) is equal to or decreased with respect to the reference value, then the atherosclerotic disease will show a rapid progression.

DETAILED DESCRIPTION OF THE INVENTION

1. Definitions

Figure 1:
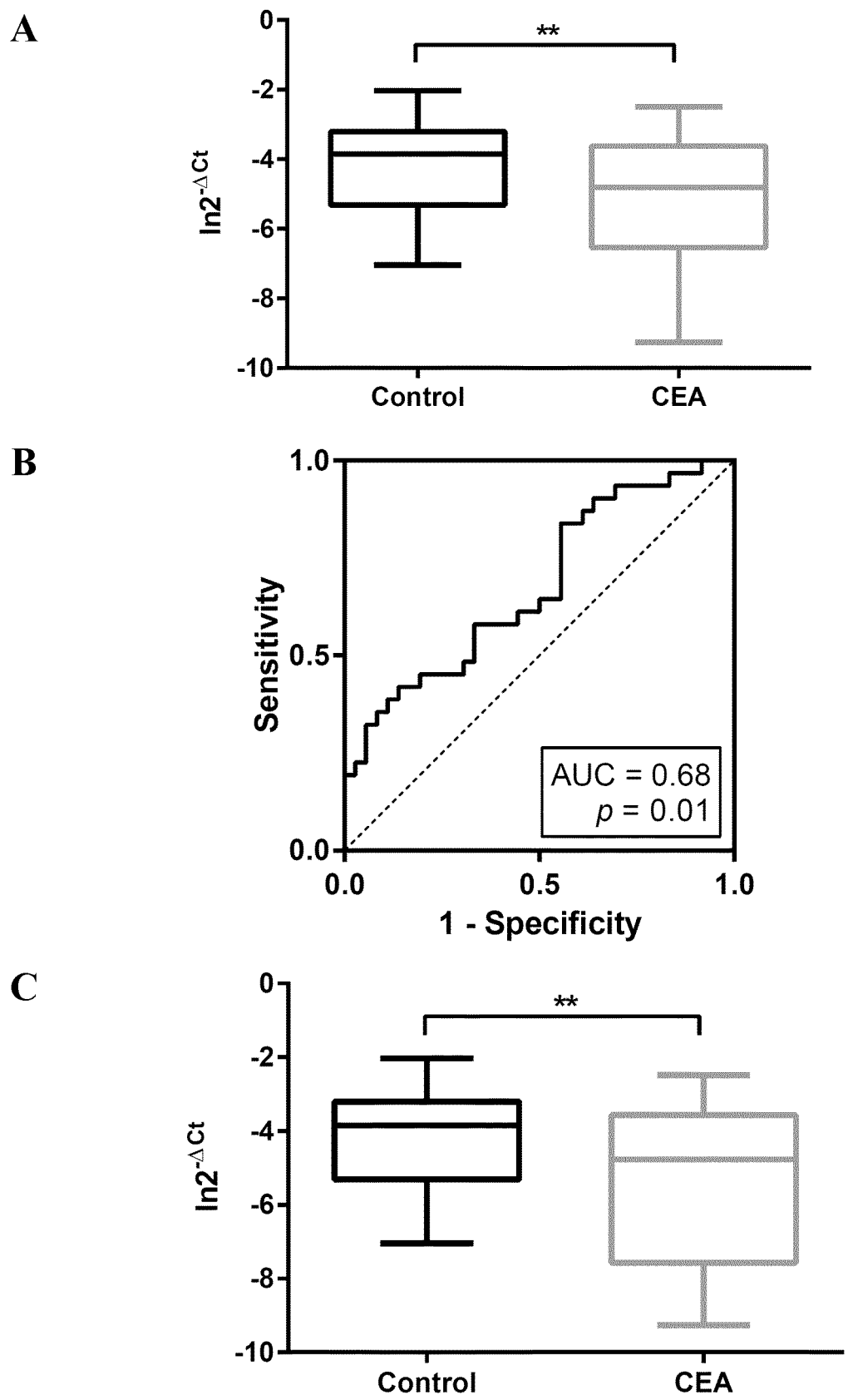
FIG. 1. Serum levels and diagnostic accuracy of miR-638 in the CEA patient group and symptomatic and stroke subgroups compared to the control non-CEA group. Serum levels of miR-638 assessed by RT-qPCR are reduced in CEA patients (n=31) (A), symptomatic CEA patients (n=22) (C), and stroke CEA patients (n=11) (E), compared to control non-CEA individuals (n=36) ( p<0.01; * p<0.001). ln $2^{-\Delta Ct}$, miR-638 levels relative to cel-miR-54, transformed into linear form using the formula $2^{-\Delta Ct}$. All quantities have been transformed using the natural logarithm. The thick black line inside the boxes indicates the median. The top and bottom of the boxes indicate $25^{th}$ percentile and $75^{th}$ percentile. Receiver-operating characteristics (ROC) analysis was used to determine the diagnostic accuracy of serum miR-638 predicting CEA intervention for high-risk ischemic stroke. (B) Discrimination of CEA patients from non-CEA control individuals, area under the curve (AUC) 0.68 (0.55 to 0.81). (D) Discrimination of symptomatic CEA patients from control non-CEA individuals, AUC 0.66 (0.52 to 0.81). (F) Discrimination of stroke CEA patients from control non-CEA individuals, AUC 0.76 (0.59 to 0.96). In all cases, the dashed lines indicate the reference line (AUC=0.5).
Figure 1:
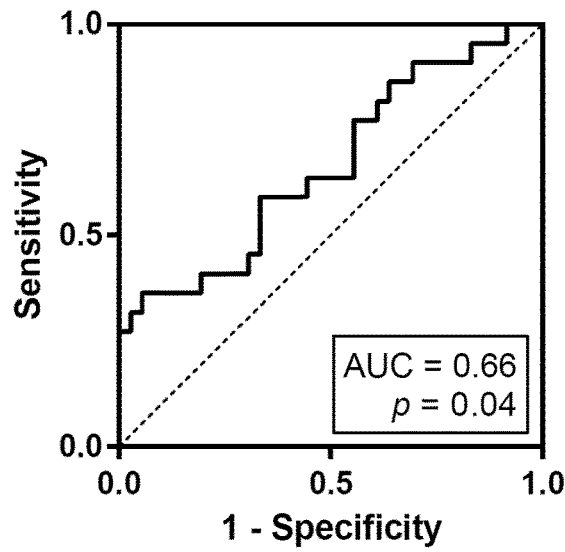
Figure 1:
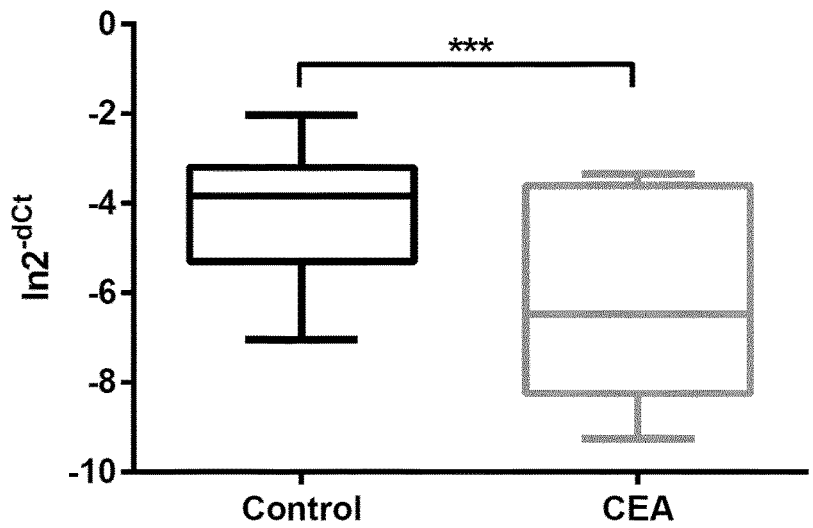
Figure 1:
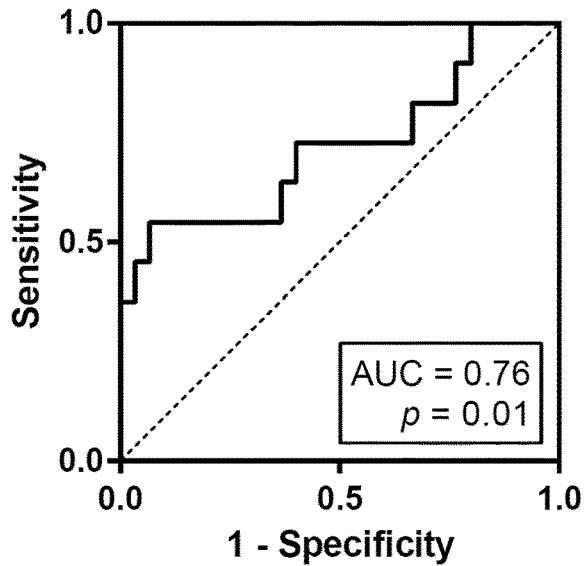

The term "amaurosis fugax", as used herein, relates to a painless transient monocular visual loss (i.e., loss of vision in one eye that is not permanent).

The term "atherosclerosis", as used herein, relates to a pathology characterized by the deposition and infiltration of lipid substances in the walls of medium- and thick-sized arteries. The cells of the arterial wall interpret this deposition as an invasion and activate circulating monocytes of the immune system, which penetrate the arterial wall, are converted into macrophages and start to phagocyte LDL particles, generating an inflammatory process. Inflammation in turn causes the multiplication and migration of the smooth muscle cells of the wall, which gradually cause narrowing of the arterial diameter. The specific thickening is referred to as an atheromatous plaque. It is the most common form of arteriosclerosis. The diseases forming atherosclerosis syndrome and characterized by involvement of the arteries through atheromatous plaques, and accordingly obstruction of blood flow or ischemia, depending on the artery of the organ involved, are ischemic heart disease (the maximum representative thereof being acute myocardial infarction, in the heart), cerebrovascular disease (in the form of stroke or cerebral thrombosis or cerebral haemorrhage, in the central nervous system), intermittent claudication (the maximum seriousness thereof being acute arterial ischemia of the lower limbs), erectile dysfunction, ischemic colitis (an area of inflammation, irritation and swelling, caused by interference with the blood flow to the colon, in the arteries of the intestines) and aortic aneurism.

The term "carotid artery disease", also known as "carotid artery stenosis", or "carotid stenosis" relates to a narrowing or constriction of the inner surface (lumen) of the carotid artery, usually caused by atherosclerosis. The blood supply to the carotid artery starts at the arch of the aorta, the carotid artery divides into the internal carotid artery (which supplies blood to the brain) and the external carotid artery. The atherosclerotic plaque usually builds up at that division of the carotid, causing the narrowing of stenosis. Methods to determine carotid artery stenosis are known by the skilled person and include, without limitation, duplex Doppler ultrasonography, arteriography, computed tomographic angiography (CTA), or magnetic resonance angiography (MRA).

The term "carotid artery stenting" or CAS, as used herein, relates to an endovascular surgery wherein a stent is deployed within the lumen of the carotid artery to prevent a stroke by treating narrowing of the carotid artery. CAS is used to treat narrowing of the carotid artery in high-risk patients, when carotid endarterectomy (CEA) is considered too risky.

The term "carotid endarterectomy" or CEA, as used herein, relates to a surgical procedure used to reduce the risk of stroke, by correcting stenosis (narrowing) in the common carotid artery or internal carotid artery. Endarterectomy involves material removal on the inside of an artery.

The term "cerebrovascular event", as used herein relates to a clinical syndrome caused by disruption of blood supply to the brain, characterized by rapidly developing signs of focal or global disturbance of cerebral functions, lasting for more than 24 hours or leading to death. A cerebrovascular event is usually known as stroke, since this is the most common cerebrovascular event. Cerebrovascular events according to the invention include transient ischemic attack (TIA), stroke and amaurosis fugax.

The term "decreased expression level", as used herein in relation to the expression level of a miRNA, particularly miR-638, relates to a situation where the level of expression of miR-638 is decreased at least 5%, at least 10%, at least 20%, at least 30%, at least 40%, at least 50%, at least 60%, at least 70%, at least 80%, at least 90% or at least 100% when compared to the corresponding reference value.

The term "determination of probability", or "predicting" as used herein in the context of the predicting methods of the invention, relates to the prediction that a subject suffers from a stroke, or relates to the prediction of the progression of atherosclerotic disease in a subject. As the persons skilled in the art will understand, such determination does not usually seek to be correct for all (i.e., 100%) of the subjects that are going to be identified. However, the term requires that a statistically significant part of the subjects can be identified (for example, a cohort in a cohort study). The person skilled in the art can easily determine if a part is statistically significant using several well-known statistical evaluation tools, for example, determination of confidence intervals, determination of p values, Student's t-test, Mann-Whitney test, etc. The details are found in Dowdy and Wearden, Statistics for Research, John Wiley and Sons, New York 1983. The preferred confidence intervals are at least 90%, at least 95%, at least 97%, at least 98% or at least 99%. The p values are preferably 0.1, 0.05, 0.01, 0.005 or 0.0001. More preferably, at least 60%, at least 70%, at least 80% or at least 90% of the subjects of a population can be suitably identified by the method of the present invention.

The term "diagnose" or "diagnosis", as used herein, relates to the evaluation of the probability according to which a subject suffers a specific pathology (in this case, suffering from unstable atherosclerotic plaque). As the skilled in the art will understand, such evaluation may not be correct for 100% of the subjects to be diagnosed, although it preferably is. The term, however, requires being able to identify a statistically significant part of the subjects.

The term "high probability", as used herein in the predicting methods of the invention, relates to the situation where the subject shows at least 5%, at least 10%, at least 20%, at least 30%, at least 40%, at least 50%, at least 60%, at least 70%, at least 80%, at least 90%, at least 100% probabilities of developing or suffering from a disease, particularly stroke or atherosclerotic disease.

The term "increased expression level", as used herein in relation to the expression level of a miRNA, particularly miR-638, relates to a situation where the level of expression of miR-638 is increased at least 5%, at least 10%, at least 20%, at least 30%, at least 40%, at least 50%, at least 60%, at least 70%, at least 80%, at least 90% or at least 100% when compared to the corresponding reference value.

The term "level of expression" relates to the measurement of the amount of a nucleic acid, e.g. RNA or mRNA, or of a protein. In the context of the invention, the level of expression relates to the measurement of the amount of a nucleic acid, particularly RNA, more particularly miRNA, even more particularly miR-638.

The term "low probability, as used herein in the predicting methods of the invention, relates to the situation where the subject shows at least 5%, at least 10%, at least 20%, at least 30%, at least 40%, at least 50%, at least 60%, at least 70%, at least 80%, at least 90%, at least 100% probabilities of not developing or suffering from a disease, particularly stroke or atherosclerotic disease.

The terms "miRNA" or "microRNA", used interchangeably herein, are endogenous RNAs, some of which are known to regulate the expression of protein-coding genes at the post-transcriptional level. As used herein, the term "miRNA" refers to any type of micro-interfering RNA, including but not limited to, endogenous microRNA and artificial microRNA. Typically, endogenous miRNAs are small RNAs encoded in the genome which are capable of modulating the productive utilization of mRNA. A mature miRNA is a single-stranded RNA molecule of about 21-23 nucleotides in length which is complementary to a target sequence, and hybridizes to the target RNA sequence to inhibit its translation. miRNAs themselves are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to down-regulate gene expression. The term "circulating miRNA", as used herein, also known as "cell-free miRNA", relates to extracellular miRNA that circulates in the bloodstream.

Pre-miRNAs are referred to as "mir", whereas mature miRNAs are referred to as "miR". This prefix is followed by a dash and a number, the latter often indicating order of naming. miRNAs with nearly identical sequences except for one or two nucleotides are annotated with an additional lower case letter. Pre-miRNAs that lead to 100% identical mature miRNAs but that are located at different places in the genome are indicated with an additional dash-number suffix. Species of origin is designated with a three-letter prefix. Nomenclature conventions used to describe miRNA sequences are described further in Ambros V et al., RNA, 2003, 9:277-279, the entire contents of which are incorporated herein by reference.

The term "miR-638", as used herein, relates to the human miRNA as defined in the miRBase database of the University of Manchester (http://www.mirbase.org/index.shtml) (release 21 as of June 2014) under accession number MIMAT0003308.

The term "reference value" or "reference level", as used herein in the context of the method of the invention, relates to a value used as a reference for the expression level values/data obtained from samples of subjects to be diagnosed with a disease, in particular an atherosclerotic disease.

The term "revascularization procedure", as used herein, relates to a procedure aimed at the restoration of perfusion to a body part or body organ that has suffered from ischemia. Revascularization procedures include, without limitation, vascular bypass, angioplasty, atherectomy, endarterectomy (including carotid endarterectomy or CEA), stenting (including carotid artery stenting or CAS). In a particular embodiment, the revascularization procedure is selected from the group consisting of CEA and CAS.

The term "sample" or "biological sample", as used herein, refers to biological material isolated from a subject. The biological sample contains any biological material suitable for detecting RNA, particularly miRNA, and is a material comprising genetic material from the subject. The biological sample can comprise cell and/or non-cell material of the subject, preferably non-cell material. In the present invention, the sample comprises genetic material, e.g., DNA, genomic DNA (gDNA), complementary DNA (cDNA), RNA, heterogeneous nuclear RNA (hnRNA), mRNA, etc., from the subject under study. In a particular embodiment, the genetic material is RNA. In a preferred embodiment the RNA is miRNA. The sample can be isolated from any suitable tissue or biological fluid such as, for example blood, saliva, plasma, serum, urine, cerebrospinal liquid (CSF), feces, a buccal or buccal-pharyngeal swab, a surgical specimen, a specimen obtained from a biopsy, and a tissue sample embedded in paraffin. Methods for isolating samples are well known to those skilled in the art.

The term "SCORE", or "systematic coronary risk evaluation", as used herein, relates to a cardiovascular disease risk assessment system initiated by the European Society of Cardiology, using data from 12 European cohort studies covering a wide geographic spread of countries at different levels of cardiovascular risks. The SCORE risk estimation is based on the following risk factors: gender, age, smoking, systolic blood pressure, total cholesterol, and estimates fatal cardiovascular disease events over a ten-year period. Determination of the SCORE risk estimation for a given individual can be carried out essentially as described by Conroy et al. (European Heart Journal (2003) 24, 987-1003).

The term "stroke", also known as cerebrovascular accident (CVA), cerebrovascular indicent (CVI), or brain attack, is used herein to relate to the situation wherein poor blood flow to the brain resulting in cell death. Ischemic stroke (also known as ischaemic infarction) is the result of lack of blood flow, as a consequence of an obstruction within a blood vessel supplying blood to the brain. Hemorrhagic stroke (also known as intracerebral hemorrhage) is due to bleeding. As a result of the stroke, the brain does not function properly. Signs and symptoms of a stroke may include an inability to move or feel on one side of the body, problems understanding or speaking, feeling like the world is spinning, or loss of vision to one side among others. Signs and symptoms often appear soon after the stroke has occurred. If symptoms last less than one or two hours it is known as a transient ischemic attack (TIA).

The term "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The term "transient ischemic attack" or TIA, as used herein, relates to a transient episode of neurologic dysfunction caused by ischemia (loss of blood flow) (either focal brain, spinal cord, or retinal) without acute infarction (tissue death). TIAs have the same underlying cause as strokes: a disruption of cerebral blood flow (CBF), and are often referred to as mini-strokes or mega-strokes.

The term "treatment", as used herein, refers to both therapeutic measures and prophylactic or preventative measures, wherein the object is to prevent or slow down (lessen) an undesired physiological change or disorder, such as a atherosclerotic disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapy", as used herein, refers to the attempted remediation of a health problem, usually following a diagnosis, or to prevention or the appearance of a health problem. As such, it is not necessarily a cure, i.e. a complete reversion of a disease. Said therapy may or may not be known to have a positive effect on a disease. This term includes both therapeutic treatment and prophylactic or preventative measures, in which the object is to prevent or stop (reduce) an undesired physiological change or disorder. For the purpose of this invention, beneficial or desired clinical results include, without limitation, relieving symptoms, reducing the spread of the disease, stabilizing pathological state (specifically not worsening), slowing down or stopping the progression of the disease, improving or mitigating the pathological state and remission (both partial and complete), both detectable and undetectable. It can also involve prolonging survival in comparison with the expected survival if treatment is not received. Those subjects needing treatment include those subjects already suffering the condition or disorder, as well as those with the tendency to suffer the condition or disorder or those in which the condition or disorder must be prevented.

The term "vascular disease risk factor", as used herein, relates to risk factors associated with coronary heart disease and stroke including unchangeable risk factors such as family history, ethnicity and age, and treatable risk factors such as tobacco exposure, smoking, hypertension (high blood pressure), peripheral vascular disease (circulation disorder affecting blood vessels outside the heart and brain), high cholesterol, obesity, physical inactivity, diabetes, unhealthy diet and harmful use of alcohol.

The term "vulnerable plaque", also known in the art as "unstable plaque", or "unstable atherosclerotic plaque" or "vulnerable atherosclerotic plaque", has been used to describe those atherosclerotic plaques (also known in the art as atheromatous plaque) that are particularly susceptible to disruption. Vulnerable plaques are generally characterized as those having a thin inflamed fibrous cap over a very large lipid core. However, only a small percentage of such plaques rupture, and plaques with different characteristics may also rupture and thrombose. Thus, a vulnerable plaque is a kind of atheromatous plaque [a collection of white blood cells (primarily macrophages) and lipids (including cholesterol) in the wall of an artery] that is particularly unstable and prone to produce sudden major problems such as a heart attack or stroke. Defining characteristics of a vulnerable plaque include inflammatory activity, thin fibrous cap, large lipid core, visible ulceration, intraplaque hemorrhage, and rupture.

2. Method for Diagnosing Unstable Atherosclerotic Plaque

The authors of the present invention have found that circulating, cell-free miRNA miR-638 is a biomarker for vulnerable atherosclerotic plaque identification in patients and, consequently, for primary and secondary ischemic stroke risk prediction, particularly in high cardiovascular risk individuals.

Thus, in a first aspect, the invention relates to a method for diagnosing unstable atherosclerotic plaque in a subject (first method of the invention, unstable plaque diagnosis method of the invention, or diagnostic method of the invention), said method comprising (i) Determining the expression level of circulating miRNA miR-638 in a sample from said subject, and (ii) Comparing the expression level obtained in (i) to a reference value, wherein if the expression level of circulating miR-638 in (i) is decreased with respect to the reference value, then the subject is diagnosed with unstable atherosclerotic plaque, or wherein if the expression level of circulating miR-638 in (i) is equal or increased with respect to the reference value, then the subject is not diagnosed with unstable atherosclerotic plaque.

In a particular embodiment, the stroke is ischemic stroke, more particularly ischemic stroke caused by carotid artery disease.

In a first step of the method of the invention for diagnosing unstable atherosclerotic plaque, the expression level of circulating cell-free miRNA miR-638 is determined in a sample from a subject whose diagnosis is to be determined.

Before analyzing the sample, it will often be desirable to perform one or more preparation operations upon said sample aimed at separating the molecule to be determined (RNA, in particular miRNA) from other molecules found in the sample. Typically, these sample preparation operations include manipulations such as concentration, suspension, extraction of intracellular material, e.g., nucleic acids from tissue/whole cell samples and the like, amplification of nucleic acids, fragmentation, transcription, labeling and/or extension reactions. Nucleic acids, especially RNA can be isolated using any techniques known in the art. There are two main methods for isolating RNA: (i) phenol-based extraction and (ii) silica matrix or glass fiber filter (GFF)-based binding. Phenol-based reagents contain a combination of denaturants and RNase inhibitors for cell and tissue disruption and subsequent separation of RNA from contaminants. Phenol-based isolation procedures can recover RNA species in the 10-200-nucleotide range e.g., miRNAs, 5S rRNA, 5.8S rRNA, and U1 snRNA. If a sample of "total" RNA was purified by the popular silica matrix column or GFF procedure, it may be depleted in small RNAs. Extraction procedures such as those using Trizol or TriReagent, however will purify all RNAs, large and small, and are the recommended methods for isolating total RNA from biological samples that will contain miRNAs/siRNAs. These methods are typically well known by a person skilled in the art. There are also commercial kits available for miRNA purification including, without limitation, miRNeasy Mini kit from Qiagen, miRNA isolation kits from Life Technologies, mirPremier microRNA isolation kit from Sigma-Aldrich and High Pure miRNA isolation kit from Roche.

The level of expression of miR-638 is determined in a sample from a subject, wherein said sample is any sample comprising nucleic acids, particularly comprising circulating miRNA, comprising without limitation a cell sample, a tissue sample, a serum sample, a urine sample, a plasma sample, a cerebrospinal fluid (CSF) sample, a saliva sample, a pleural fluid sample, a sinovial fluid sample. The sample can be obtained by any conventional method depending on the sample to be analyzed. Methods for obtaining said samples are routinary and known by the skilled person. In a particular embodiment, the sample is a cell-free sample. In a preferred embodiment, the sample is a serum sample.

Determination of the levels of RNA, in particular the levels of miRNA, can be carried out by any method known in the art such as qPCR, northern blot, RNA dot blot, TaqMan, tag based methods such as serial analysis of gene expression (SAGE) including variants such as LongSAGE and SuperSAGE, microarrays. Determination of the mRNA levels can also be carried out by fluorescence in situ hybridization (FISH). The detection can be carried out in individual samples or in tissue microarrays. In a particular embodiment, the expression levels of miR-638 in a sample from a subject to be diagnosed with unstable atherosclerotic plaque are determined by real-time PCR (RT-PCR).

In order to normalize the values of expression of miRNA among the different samples, it is possible to compare the expression levels of the miRNA of interest in the test samples with the expression of a control RNA. Thus, in the context of the invention, the term "normalized" expression level refers to the expression level of a miRNA, particularly miR-638, relative to the expression level of a single reference gene or control RNA, or a particular set of reference or control RNAs. A "control RNA" as used herein, relates to RNA whose expression level does not change or changes only in limited amounts in samples under analysis with respect to control samples. In the analysis of circulating miRNAs, various strategies van be used for data normalization, ranging from the use of particular endogenous miRNA or small RNA controls, external spike-in molecules or measures of central tendency. When quantifying cellular miRNAs, stable small RNA controls are currently used as reference RNAs. These include small noncoding RNAs, and specifically small nuclear RNA and small nucleolar RNA such as SNORD44 (RNU44), SNORD48 (RNU48) and RNU6-1 (Mamm U6). For serum miRNAs, there is growing evidence that the above-mentioned small RNAs are highly variable or not stably detectable, thus leading to the search for suitable stable control miRNAs that are firmly detectable in human serum. The most common choice could be the use of a miRNA that does not vary considerably between individuals. In a preferred embodiment, a synthetic miRNA is spiked into their RNA prep to help monitor RNA recovery and reverse transcription efficiency. Examples of spike-in controls are C. elegans cel-miR-39 or cel-miR-54 miRNA mimics, that can be easily detected by real-time RT-PCR. In one embodiment, relative miRNA expression quantification is calculated according to the comparative threshold cycle (Ct) method using cel-miR-54 or cel-miR-39 as spike-in controls. Final results are determined according to the formula 2-ΔCt, where ΔCT values of the sample are determined by subtracting the Ct value of the target gene from the value of the control miRNA.

In a second step of the method of the invention for diagnosing unstable atherosclerotic plaque, the level of expression of circulating miR-638 in a sample from a subject whose diagnosis is to be determined is compared to a reference value, wherein if the expression level of miR-638 is decreased with respect to the reference value, then the subject is diagnosed with unstable atherosclerotic plaque, or wherein if the level of expression of circulating miR-638 is equal or increased with respect to the reference value, then the subject is not diagnosed with unstable atherosclerotic plaque.

The reference value or reference level according to the any of the methods of the invention can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested. Various considerations are taken into account when determining the reference value of the marker. Among such considerations are the age, weight, sex, general physical condition of the patient and the like. For example, equal amounts of a group of at least 2, at least 10, at least 100 to preferably more than 1000 subjects, preferably classified according to the foregoing considerations, for example according to various age categories, are taken as the reference group.

In a particular embodiment of the diagnostic method of the invention, the reference value is the expression level of the miR-638 determined in a sample from a control subject, wherein the control subject is a healthy subject or a subject who has not been diagnosed with unstable atherosclerotic plaque. In another embodiment, the reference value is the expression level of the miR-638 as an average value determined in a pool of healthy subjects or in a pool of subjects who have not been diagnosed with unstable atherosclerotic plaque. Said reference value sample is typically obtained by combining equal amounts of samples from a subject population. In a particular preferred embodiment, the reference value is the expression level of miR-638 determined in a sample from a control subject, wherein said control subject shows a degree of carotid stenosis that is equal to or lower than 30%. Methods to determine carotid artery stenosis are known by the skilled person and include, without limitation, duplex Doppler ultrasonography, arteriography, computed tomographic angiography (CTA), or magnetic resonance angiography (MRA). In a more particular embodiment, the reference value is the expression level of the miR-638 determined in a sample from a control subject, wherein said control subject shows a degree of carotid stenosis that is equal to or lower than 30%, and wherein said subject has not suffered from ischemic stroke or from atherosclerosis, particularly from carotid atherosclerosis. In a particular embodiment, the control subject shows a SCORE equal to or higher than 5.

Once the reference value of miR-638 expression is established, the expression levels of circulating miR-638 expressed in a sample from a subject to be diagnosed can be compared with this reference value, and thus be assigned as "increased", "decreased" or "equal". For example, an increase in expression levels above the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value is considered as "increased" expression level. On the other hand, a decrease in expression levels below the reference value of at least 0.9-fold, 0.75-fold, 0.2-fold, 0.1-fold, 0.05-fold, 0.025-fold, 0.02-fold, 0.01-fold, 0.005-fold or even less compared with reference value is considered as "decreased" expression level. Expression levels can be seen as "equal" to the reference value if the levels differ with respect to the reference value less than 5%, less than 4%, less than 3%, less than 2%, less than 1%, less than 0.5%, less than 0.4%, less than 0.3%, less than 0.1%, less than 0.05%, or less.

Thus, according to the diagnostic method of the invention, if there is a decrease in the expression level of circulating miR-638 in a sample of a subject whose diagnosis is to be determined with respect to the reference value, then said subject is diagnosed with unstable atherosclerotic plaque. If there is no change or an increase in the expression level of circulating miR-638 in a sample of a subject whose diagnosis is to be determined with respect to the reference value, then said subject is not diagnosed with unstable atherosclerotic plaque.

The person skilled in the art will understand that the diagnosis may not be correct for 100% of patients under study. However, the expression requires that the diagnosis method provides correct results for a statistically significant portion of patients. Determination whether the method of the invention provides statistically significant predictions can be carried out by using standard statistical techniques such as the determination of confidence intervals, determination of p value, Student's t-test, Mann-Whitney test. Suitable confidence intervals are at least 50%, at least 60%, at least 70%, at least 80%, at least 90%, at least 95%. p values are, preferably, 0.05, 0.01, 0.005.

In a particular embodiment, the subject whose diagnosis is to be determined according to the first method of the invention has already suffered from a cerebrovascular event previously to being diagnosed with unstable atherosclerotic plaque. In a particular embodiment, said cerebrovascular event is selected from the group consisting of transient ischemic attack (TIA), stroke, and amaurosis fugax.

In a particular alternative embodiment, the subject whose diagnosis is to be determined according to the first method of the invention has not suffered from a cerebrovascular event previously to being diagnosed with unstable atherosclerotic plaque. In this case, the method of the invention further comprises determination of at least one vascular disease risk factor. Vascular disease risk factors are known in the art and include, without limitation, tobacco exposure, smoking, hypertension, peripheral vascular disease, high cholesterol, obesity, physical inactivity, diabetes, unhealthy diet and harmful use of alcohol. In a particular embodiment, the at least one vascular disease risk factor that is additionally determined is selected from the group consisting of smoking, diabetes, peripheral vascular disease and combinations thereof. Thus, according to the diagnosis method of the invention, if the subject shows at least two vascular disease risk factors, particularly wherein said risk factors are selected from the group consisting of smoking, diabetes, and peripheral vascular disease, then the subject is diagnosed with unstable atherosclerotic plaque.

In a particular embodiment of the diagnostic method of the invention, the systematic coronary risk evaluation (SCORE) is additionally determined. Therefore, when the SCORE is additionally determined according to the diagnostic method of the invention, and wherein said SCORE is equal to or higher than 5, then the subject is diagnosed with unstable atherosclerotic plaque.

In a particular embodiment of the diagnostic method of the invention, the carotid stenosis grade of the subject whose diagnosis is to be determined is additionally determined. Therefore, when the carotid stenosis grade of the subject to be diagnosed is additionally determined according to the diagnostic method of the invention, if the subject suffers from high grade carotid stenosis, then the subject is diagnosed with unstable atherosclerotic plaque.

3. Method for Determining the Probability of Stroke

The presence of unstable atherosclerotic plaque is associated with an increased risk of suffering a stroke. Accordingly, the levels of cell-free miRNA miR-638, which can be used as marker for the presence of unstable atherosclerotic plaque can also be used as marker for determining the risk of suffering stroke, particularly in individuals having high risk of a cardiovascular disease.

Thus, in another aspect, the invention relates to a method for determining the probability that a subject suffers from a stroke (second method of the invention, or stroke probability prediction method of the invention), said method comprising (i) Determining the expression level of circulating miRNA miR-638 in a sample from said subject, and (ii) Comparing the expression level obtained in (i) to a reference value, wherein if the expression level of circulating miR-638 in (i) is decreased with respect to the reference value, then the subject shows a high probability of suffering from a stroke, or wherein if the expression level of circulating miR-638 in (i) is equal or increased with respect to the reference value, then the subject shows a low probability of suffering from a stroke.

In a particular embodiment, the stroke is ischemic stroke, more particularly ischemic stroke caused by carotid artery disease.

In a first step of the second method of the invention, the expression level of circulating miRNA miR-638 is determined in a sample from a subject whose probability of suffering from a stroke is to be determined.

Methods to determine the level of expression of a miRNA, particularly miR-638, have been described previously in the context of the diagnostic method of the invention and incorporated herein. In a particular embodiment, miRNA expression levels, particularly miR-638 levels, are determined by RT-PCR.

Suitable samples to determine miRNA expression levels, particularly miR-638 levels, have been described previously in the context of the diagnostic method of the invention and incorporated herein. In a particular embodiment, the sample is a serum sample.

In a second step of the second method of the invention, the level of expression of circulating miR-638 in a sample from a subject whose stroke probability is to be determined is compared to a reference value, wherein if the expression level of circulating miR-638 is decreased with respect to the reference value, then the subject shows a high probability of suffering from a stroke, and wherein if the expression level of circulating miR-638 is equal or increased with respect to the reference value, then the subject shows a low probability of suffering from a stroke.

In a particular embodiment of the stroke probability prediction method of the invention, the reference value is the expression level of the miR-638 determined in a sample from a control subject, wherein the control subject is a healthy subject or a subject who has not suffered from a stroke. In another embodiment, the reference value is the expression level of the miR-638 as an average value determined in a pool of healthy subjects or in a pool of subjects who have not suffered from stroke. Said reference value sample is typically obtained by combining equal amounts of samples from a subject population. In a particular preferred embodiment, the reference value is the expression level of miR-638 determined in a sample from a control subject, wherein said control subject shows a degree of carotid stenosis that is equal to or lower than 30%. Methods to determine carotid artery stenosis have been cited in the context of the first method of the invention and incorporated herein. In a more particular embodiment, the reference value is the expression level of the miR-638 determined in a sample from a control subject, wherein said control subject shows a degree of carotid stenosis that is equal to or lower than 30%, and wherein said subject has not suffered from ischemic stroke or from atherosclerosis, particularly from carotid atherosclerosis. In a particular embodiment, the control subject shows a SCORE equal to or higher than 5.

Once the reference value of miR-638 expression is established, the expression levels of circulating miR-638 expressed in a sample from a subject whose stroke probability is to be determined can be compared with this reference value, and thus be assigned a level of "increased" or "decreased", as indicated above in the context of the first method of the invention.

Thus, according to the second method of the invention, if there is a decrease in the expression level of circulating miR-638 in a sample of a subject whose stroke probability is to be determined with respect to the reference value, then said subject shows a high probability of suffering from a stroke. If there is no variation or an increase in the expression level of circulating miR-638 in a sample of a subject whose stroke probability is to be determined with respect to the reference value, then said subject shows a low probability of suffering from a stroke.

A high probability of developing a stroke is understood to mean the situation where the subject shows at least 5%, at least 10%, at least 20%, at least 30%, at least 40%, at least 50%, at least 60%, at least 70%, at least 80%, at least 90%, at least 100% probabilities of suffering from stroke over time.

A low probability of developing a stroke is understood to mean the situation where the subject shows at least 5%, at least 10%, at least 20%, at least 30%, at least 40%, at least 50%, at least 60%, at least 70%, at least 80%, at least 90%, at least 100% probabilities of not suffering from stroke over time.

The person skilled in the art will understand that the prediction may not be correct for 100% of patients under study. However, the expression requires that the prediction method provides correct results for a statistically significant portion of patients. Determination whether the method of the invention provides statistically significant predictions can be carried out by using standard statistical techniques such as the determination of confidence intervals, determination of p value, Student's t-test, Mann-Whitney test. Suitable confidence intervals are at least 50%, at least 60%, at least 70%, at least 80%, at least 90%, at least 95%. p values are, preferably, 0.05, 0.01, 0.005.

In a particular embodiment, the subject whose stroke probability is to be determined according to the second method of the invention has already suffered from a cerebrovascular event. In a particular embodiment, said cerebrovascular event is selected from the group consisting of transient ischemic attack (TIA), stroke, and amaurosis fugax.

In a particular alternative embodiment, the subject whose stroke probability is to be determined according to the second method of the invention has not suffered from a cerebrovascular event previously. In this case, the method of the invention further comprises determination of at least one vascular disease risk factor. Vascular disease risk factors have been mentioned before in the context of the first method of the invention and incorporated herein. In a particular embodiment, the at least one vascular disease risk factor that is additionally determined is selected from the group consisting of smoking, diabetes, peripheral vascular disease and combinations thereof, wherein said factors are considered as positive as follows:

Smoking: A smoker patient is defined as any person who smoked any cigarette in the last month. Ex-smoker is defined as any person who had not smoked any cigarette in the last 6-12 months Diabetes: Diabetes is a chronic disease associated with abnormally high levels of the sugar glucose in the blood. Diabetes is due to one of two mechanisms: 1) Inadequate production of insulin (which is made by the pancreas and lowers blood glucose), or 2) Inadequate sensitivity of cells to the action of insulin. The two main types of diabetes correspond to these two mechanisms and are called insulin dependent (type 1) and non-insulin dependent (type 2) diabetes. The following criteria for diagnosis are used:

Fasting plasma glucose level ≥7.0 mmol/l (126 mg/dl).

Plasma glucose ≥11.1 mmol/l (200 mg/dl) two hours after a 75 g oral glucose load as in a glucose tolerance test.

Symptoms of high blood sugar and casual plasma glucose ≥11.1 mmol/l (200 mg/dl).

Glycated hemoglobin (HbA$_{1C}$)≥48 mmol/mol (≥6.5 DCCT %).

Peripheral vascular disease: Is defined as a presence of atheroma (fatty deposits) in the walls of the arteries leading to insufficient blood flow to the muscles and other tissues. This can be symptomatic or asymptomatic. Peripheral vascular disease is a manifestation of systemic atherosclerosis that leads to significant narrowing of arteries distal to the arch of the aorta. The most common symptom of peripheral vascular disease is intermittent claudication. At other times, peripheral vascular disease leads to acute or critical limb ischemia. Intermittent claudication manifests as pain in the muscles of the legs with exercise; it is experienced by 2 percent of persons older than 65 years. Physical findings include abnormal pedal pulses, femoral artery bruit, delayed venous filling time, cool skin, and abnormal skin color. Most patients present with subtle findings and lack classic symptoms, which makes the diagnosis difficult. The standard office-based test to determine the presence of peripheral vascular disease is calculation of the ankle-brachial index. Magnetic resonance arteriography, duplex scanning, and hemodynamic localization are noninvasive methods for lesion localization and may be helpful when symptoms or findings do not correlate with the ankle-brachial index. Contrast arteriography is used for definitive localization before intervention.

Thus, according to the stroke prediction method of the invention, if the subject shows at least two vascular disease risk factors, particularly wherein said risk factors are selected from the group consisting of smoking, diabetes, and peripheral vascular disease, then the subject shows a high probability of suffering from stroke.

In a particular embodiment of the stroke probability prediction method of the invention, the systematic coronary risk evaluation (SCORE) is additionally determined, wherein if SCORE is equal to or higher than 5, then the subject shows a high probability of suffering from stroke.

In a particular embodiment of the stroke probability prediction method of the invention, the carotid stenosis grade of the subject whose diagnosis is to be determined is additionally determined, wherein if the subject suffers from high grade carotid stenosis, then the subject shows a high probability of suffering from stroke.

4. Method for Selecting a Therapy for a Subject Suffering from Carotid Artery Disease Given the role of miR-638 as a marker for unstable atherosclerotic plaque, in unstable atherosclerotic plaque in the carotid artery, and given that the treatment of choice for unstable atherosclerotic plaque in the carotid is the revascularizacion procedure, the levels of miR-638 can also be used for selecting patients which require such a therapy or for selecting a therapy for patients having unstable atherosclerotic plaque. Thus, in another aspect, the invention relates to a method for the selection of a therapy for a subject suffering from carotid artery disease (third method of the invention, or therapy selection method of the invention) that comprises (i) Determining the expression level of circulating miRNA miR-638 in a sample from said subject, and (ii) Comparing the expression level obtained in (i) to a reference value, wherein if the expression level of circulating miR-638 in (i) is decreased with respect to the reference value, then a therapy comprising a revascularization procedure is selected.

In a particular embodiment, the revascularization procedure according to the third method of the invention is selected from the group consisting of carotid endarterectomy (CEA) or carotid artery stenting (CAS).

In a first step of the third method of the invention, the expression level of circulating miRNA miR-638 is determined in a sample from a subject suffering from carotid artery disease for whom therapy is to be selected.

Methods to determine the level of expression of a miRNA, particularly miR-638, have been described previously in the context of the diagnostic method of the invention and incorporated herein. In a particular embodiment, miRNA expression levels, particularly miR-638 levels, are determined by RT-PCR.

Suitable samples to determine miRNA expression levels, particularly miR-638 levels, have been described previously in the context of the diagnostic method of the invention and incorporated herein. In a particular embodiment, the sample is a serum sample.

In a second step of the third method of the invention, the level of expression of circulating miR-638 in a sample from a subject suffering from carotid artery disease for whom therapy is to be selected is compared to a reference value, wherein if the expression level of circulating miR-638 is decreased with respect to the reference value, then a therapy comprising a revascularization procedure is selected.

In a particular embodiment of the therapy selection method of the invention, the reference value is the expression level of the miR-638 determined in a sample from a control subject, wherein the control subject is a healthy subject or a subject who has not suffered from a stroke or a subject who has not suffered from unstable atherosclerotic plaque or a subject who has not suffered from carotid artery disease. In another embodiment, the reference value is the expression level of the miR-638 as an average value determined in a pool of healthy subjects or in a pool of subjects who have not suffered from stroke, unstable atherosclerotic plaque or carotid artery disease. Said reference value sample is typically obtained by combining equal amounts of samples from a subject population. In a particular preferred embodiment, the reference value is the expression level of miR-638 determined in a sample from a control subject, wherein said control subject shows a degree of carotid stenosis that is equal to or lower than 30%. Methods to determine carotid artery stenosis have been cited in the context of the first method of the invention and incorporated herein. In a more particular embodiment, the reference value is the expression level of the miR-638 determined in a sample from a control subject, wherein said control subject shows a degree of carotid stenosis that is equal to or lower than 30%, and wherein said subject has not suffered from ischemic stroke, from atherosclerosis, particularly from carotid atherosclerosis, or from carotid artery disease. In a particular embodiment, the control subject shows a SCORE equal to or higher than 5.

Once the reference value of miR-638 expression is established, the expression levels of circulating miR-638 expressed in a sample from a subject suffering from carotid artery disease for whom therapy is to be selected can be compared with this reference value, and thus be assigned a level of "increased" or "decreased", as indicated above in the context of the first method of the invention.

Thus, according to the third method of the invention, if there is a decrease in the expression level of circulating miR-638 in a sample of a subject suffering from carotid artery disease for whom therapy is to be selected with respect to the reference value, then a therapy comprising a pharmacological treatment or a revascularization procedure is selected. If there is no change or an increase in the expression level of circulating miR-638 in a sample of a subject suffering from carotid artery disease for whom therapy is to be selected with respect to the reference value, then no therapy comprising a pharmacological treatment or a revascularization procedure is selected.

The person skilled in the art will understand that the determination may not be correct for 100% of patients under study. However, the expression requires that the method provides correct results for a statistically significant portion of patients. Determination whether the method of the invention provides statistically significant determinations can be carried out by using standard statistical techniques such as the determination of confidence intervals, determination of p value, Student's t-test, Mann-Whitney test. Suitable confidence intervals are at least 50%, at least 60%, at least 70%, at least 80%, at least 90%, at least 95%. p values are, preferably, 0.05, 0.01, 0.005.

In a particular embodiment, the subject suffering from carotid artery disease for whom therapy is to be selected according to the third method of the invention has already suffered from a cerebrovascular event. In a particular embodiment, said cerebrovascular event is selected from the group consisting of transient ischemic attack (TIA), stroke, and amaurosis fugax.

In a particular alternative embodiment, the subject suffering from carotid artery disease for whom therapy is to be selected according to the third method of the invention has not suffered from a cerebrovascular event previously. In this case, the third method of the invention further comprises determination of at least one vascular disease risk factor. Vascular disease risk factors have been mentioned before in the context of the first method of the invention and incorporated herein. In a particular embodiment, the at least one vascular disease risk factor that is additionally determined is selected from the group consisting of smoking, diabetes, peripheral vascular disease and combinations thereof. Thus, according to the third method of the invention, if the subject shows at least two vascular disease risk factors, particularly wherein said risk factors are selected from the group consisting of smoking, diabetes, and peripheral vascular disease, then a therapy comprising a revascularization procedure is selected.

In a particular embodiment of the third method of the invention, the systematic coronary risk evaluation (SCORE) is additionally determined, wherein if SCORE is equal to or higher than 5, then a therapy comprising a revascularization procedure is selected.

In a particular embodiment of the third method of the invention, the carotid stenosis grade of the subject for whom therapy is to be selected is additionally determined, wherein if the subject suffers from high grade carotid stenosis, then a therapy comprising a revascularization procedure is selected.

5. Method for Predicting the Progression of Atherosclerotic Disease

The authors of the present invention have shown that the levels of miR-638 are not only useful for the diagnosis of an existing cardiovascular disease in the form of unstable atherosclerotic plaque, but also that this marker can be monitored after the subject has undergone a revascularization procedure and that the change with time of the levels of the marker predict whether the atherosclerotic disease is reappearing in the subject or not. Thus, in another aspect, the invention relates to a method for predicting the progression of atherosclerotic disease in a subject known to have suffered from said disease and who has undergone a revascularization procedure (atherosclerotic disease progression predictive method of the invention, or fourth method of the invention), wherein the method comprises (i) Determining the expression level of circulating miRNA miR-638 in a sample from said subject, and (ii) Comparing the expression level obtained in (i) to a reference value, wherein if the expression level of miR-638 in (i) is increased with respect to a reference value, then the atherosclerotic disease will show a slow progression, or wherein if the expression level of miR-638 in (i) is equal to or decreased with respect to the reference value, then the atherosclerotic disease will show a rapid progression.

Therefore, the fourth method of the invention is aimed at the prediction of the progression of an atherosclerotic disease in a subject, wherein said subject is known to have suffered from said disease and has undergone a revascularization procedure. In a particular embodiment, the atherosclerotic disease is selected from the group consisting of carotid artery disease, stroke, amaurosis fugax, TIA and restenosis.

In a particular embodiment, the subject for whom the progression of the atherosclerotic disease is to be predicted is additionally following a pharmacological treatment. In a more particular embodiment, said subject is follows a pharmacological treatment selected from the group consisting of an anti-platelet treatment, a cholesterol-reducing treatment, a blood pressure-lowering treatment, and a smoking cessation therapy.

Anti-platelet treatments according to the invention include treatments aimed at decreasing platelet aggregation and inhibiting thrombus formation and include, without limitation:

- irreversible cyclooxygenase inhibitors such as aspirin or triflusal (Digren),
- adenosine diphosphate (ADP) receptor inhibitors such as clopidogrel (Plavix), prasugrel (Effient), ticagrelor (Brilinta) or ticlopidine (Ticlid),
- phosphodiesterase inhibitors such as cilostazol (Pletal),
- protease-activated receptor-1 (PAR-1) antagonists such as vorapaxar (Zontivity),
- glycoprotein IIB/IIIA inhibitors such as abciximab (ReoPro), eptifibatide (Integrilin) or tirofiban (Aggrastat),
- adenosine reuptake inhibitors such as dipyridamole (Persantine), and
- thromboxane inhibitors including thromboxane synthase inhibitors and thromboxane receptor antagonists (such as Terutroban).

Cholesterol-reducing treatments according to the invention include, without limitation,

- HMG-COA reductase inhibitors including statins such as atorvastatin (Lipitor), fluvastatin (Lescol), lovastatin (Mevacor, Altoprev), pravastatin (Pravachol), rosuvastatin calcium (Crestor) or simvastatin (Zocor),
- Selective cholesterol absorption inhibitors such as ezetimibe (Zetia),
- Bile acid sequestrants such as cholestyramine (Questran, Questran Light, Prevalite, Locholest, Locholest Light), Colestipol (Colestid), or colesevelam HCl (WelChol®),
- Lipid-lowering therapies such as fibrates including gemfibrozil (Lopid), fenofibrate (Antara, Lofibra, Tricor, and Triglide) and clofibrate (Atromid-S); nicotinic acid; omega-3 fatty acid ethyl esters including Lovaza and Vascepa; and marine-derived omega-3 polyunsaturated fatty acids (PUFA).

Blood pressure-lowering treatments according to the invention include, without limitation:

- Diuretics, including chlorthalidone (Hygroton), chlorothiazide (Diuril), furosemide (Lasix), hydrochlorothiazide (Esidrix, Hydrodiuril, Microzide), indapamide (Lozol), metolazone (Mykrox, Zaroxolyn), amiloride hydrochloride (Midamar), spironolactone (Aldactone), triamterene (Dyrenium), bumetanide (Bumex),
- Beta-blockers, including acebutolol (Sectral), atenolol (Tenormin), betaxolol (Kerlone), bisoprolol fumarate (Zebeta), carteolol hydrochloride (Cartrol), metoprolol tartrate (Lopressor), metoprolol succinate (Toprol-XL), nadolol (Corgard), penbutolol sulfate (Levatol), pindolol (Visken), propranolol hydrochloride (Inderal), solotol hydrochloride (Betapace), timolol maleate (Blocadren),
- ACE (angiotensin-converting enzyme) inhibitors, including benazepril hydrochloride (Lotensin), captopril (Capoten), enalapril maleate (Vasotec), fosinopril sodium (Monopril), Lisinopril (Prinivel, Zestril), moexipril (Univasc), perindopril (Aceon), quinapril hydrochloride (Accupril), ramipril (Altace), and trandolapril (Mavik),
- Angiotensin II receptor blockers, candesartan (Atacand), eprosartan mesylate (Teveten), irbesarten (Avapro), losartan potassium (Cozaar), telmisartan (Micardis), valsartan (Diovan),
- Calcium channel blockers, including amlodipine besylate (Norvasc, Lotrel), bepridil (Vasocor), diltiazem hydrochloride (Cardizem CD, Cardizem SR, Dilacor XR, Tiazac), felodipine (Plendil), isradipine (DynaCirc, DynaCirc CR), nicardipine (Cardene SR), nifedipine (Adalat CC, Procardia XL), nisoldipine (Sular), verapamil hydrochloride (Calan SR, Covera HS, Isoptin SR, Verelan),
- Alpha blockers, including doxazosin mesylate (Cardura), prazosin hydrochloride (Minipress) and terazosin hydrochloride (Hytrin),
- Alpha-2 receptor agonists, including methyldopa,
- Combined alpha and beta-blockers, including carvedilol (Coreg), and labetalol hydrochloride (Normodyne, Trandate),
- Central agonists, including alpha methyldopa (Aldomet), clonidine hydrochloride (Catapres), guanabenz acetate (Wytensin), and guanfacine hydrochloride (Tenex),
- Peripheral adrenergic inhibitors guanadrel (Hylorel), guanethidine monosulfate (Ismelin), and reserpine (Serpasil),
- Vasodilators including hydralazine hydrocholoride (Apresoline) and minoxidil (Loniten)

Smoking cessation therapies according to the invention include, without limitation, bupropion (Zyban) and varenicline (Champix).

In a first step of the fourth method of the invention, the expression level of circulating miRNA miR-638 is determined in a sample from a subject for whom progression of atherosclerotic disease is to be predicted.

Methods to determine the level of expression of a miRNA, particularly miR-638, have been described previously in the context of the diagnostic method of the invention and incorporated herein. In a particular embodiment, miRNA expression levels, particularly miR-638 levels, are determined by RT-PCR.

Suitable samples to determine miRNA expression levels, particularly miR-638 levels, have been described previously in the context of the diagnostic method of the invention and incorporated herein. In a particular embodiment, the sample is a serum sample.

In a second step of the fourth method of the invention, the level of expression of circulating miR-638 in a sample from a subject for whom progression of atherosclerotic disease is to be predicted is compared to a reference value, wherein if the expression level of circulating miR-638 is decreased with respect to the reference value, then a therapy comprising a revascularization procedure is selected. Alternatively, if the expression level of circulating miR-638 is increased or is similar with respect to the reference value, then a therapy comprising a revascularization procedure is not selected.

In a particular embodiment of the method according to the invention to predict progression of atherosclerotic disease, the reference value is the expression level of the miR-638 determined in a sample from the subject for whom progression of atherosclerotic disease is to be predicted and determined before the revascularization procedure and/or before administration of the pharmacological treatment.

Once the reference value of miR-638 expression is established, the expression levels of circulating miR-638 expressed in a sample from a subject whose stroke probability is to be determined can be compared with this reference value, and thus be assigned a level of "increased" or "decreased", as indicated above in the context of the first method of the invention.

Thus, according to the fourth method of the invention, if there is an increase in the expression level of circulating miR-638 in a sample of a subject for whom progression of atherosclerotic disease is to be predicted with respect to the reference value, then the atherosclerotic disease will show a slow progression. If there is a decrease or no change in the expression level of circulating miR-638 in a sample of a subject for whom progression of atherosclerotic disease is to be predicted with respect to the reference value, then the atherosclerotic disease will show a rapid progression.

A slow progression of an atherosclerotic disease is understood as no increase of luminal stenosis (internal carotid artery stenosis) serially imaged by duplex ultrasound (EcoDoppler) at 6 and 12-month after diagnosis.

A rapid progression of an atherosclerotic disease is understood as an increase of luminal stenosis (internal carotid artery stenosis) serially imaged by duplex ultrasound (EcoDoppler) at 6 and 12-month after diagnosis. Alternatively, a rapid progression of an atherosclerotic disease is understood as (i) a reduction in the diameter in at least one preexisting stenosis of 10-50%, (ii) a reduction in the diameter in at least one preexisting stenosis of 30-50% or (iii) progression of a lesion to total occlusion within few months.

The person skilled in the art will understand that the prediction may not be correct for 100% of patients under study. However, the expression requires that the prediction method provides correct results for a statistically significant portion of patients. Determination whether the method of the invention provides statistically significant predictions can be carried out by using standard statistical techniques such as the determination of confidence intervals, determination of p value, Student's t-test, Mann-Whitney test. Suitable confidence intervals are at least 50%, at least 60%, at least 70%, at least 80%, at least 90%, at least 95%. p values are, preferably, 0.05, 0.01, 0.005.

In a particular embodiment, the fourth method of the invention further comprises the determination of vascular disease risk factors. Said vascular disease risk factors have been previously mentioned in the context of the first method of the invention and incorporated herein. In a particular embodiment, the vascular disease risk factor that is additionally determined according to the fourth method of the invention is smoking.

In a particular alternative embodiment of method for predicting progression of an atherosclerotic disease according to the invention, the reference value is the expression level of the miR-638 determined in a sample from a control subject, wherein the control subject is a healthy subject or a subject who has not suffered from an atherosclerotic disease. In another embodiment, the reference value is the expression level of the miR-638 as an average value determined in a pool of healthy subjects or in a pool of subjects who have not suffered from an atherosclerotic disease. Said reference value sample is typically obtained by combining equal amounts of samples from a subject population. In a particular preferred embodiment, the reference value is the expression level of miR-638 determined in a sample from a control subject, wherein said control subject shows a degree of carotid stenosis that is equal to or lower than 30%. Methods to determine carotid artery stenosis have been cited in the context of the first method of the invention and incorporated herein. In a more particular embodiment, the reference value is the expression level of the miR-638 determined in a sample from a control subject, wherein said control subject shows a degree of carotid stenosis that is equal to or lower than 30%, and wherein said subject has not suffered from an atherosclerotic disease. In a particular embodiment, the control subject shows a SCORE equal to or higher than 5.

Accordingly, when the reference value is the expression level of the miR-638 as indicated above, if there is no change or a decrease in the expression level of circulating miR-638 in a sample of a subject for whom progression of atherosclerotic disease is to be predicted with respect to the reference value, then the atherosclerotic disease will show a rapid progression. If there is an increase in the expression level of circulating miR-638 in a sample of a subject for whom progression of atherosclerotic disease is to be predicted with respect to the reference value, then the atherosclerotic disease will show a low progression. The term "no change" or "similar", in relation to expression levels of circulating miR-638, relates to any level of expression of said miRNA in a sample similar to that level of expression in the reference value. Thus, the levels are considered to be similar to those levels of the reference value when they differ in less than 5%, less than 4%, less than 3%, less than 2%, less than 1%, or less than 0.5%.

Furthermore, the invention relates to the following aspects:

The invention is detailed below by means of the following examples which are merely illustrative and by no means limiting the scope of the invention.

Example 1

Methods

Subjects and Clinical Evaluation

The inventors prospectively collected serum samples from Caucasian patients who underwent CEA (n=31) for symptomatic (transient ischemic attack (TIA), amaurosis fugax or ipsilateral stroke), or asymptomatic (absence of cerebrovascular events) stenosis. These patients had high-grade degree of carotid stenosis (>60% on EcoDoppler imaging confirmed by angio-RM or angio-TC, according to NASCET criteria). All symptomatic patients underwent CEA within three weeks from the symptomatic event. According to morphological and histological criteria, all CEA extracted plaques had instability features such as inflammatory activity, thin fibrous cap, large lipid core, visible ulceration, intraplaque hemorrhage and rupture. Control group (n=36) included age- and sex-matched patients visited at the emergency unit, without stroke history or carotid atherosclerosis (all patients presented with <30% stenosis on carotid EcoDoppler imaging). Patients with a known history of acute arterial or venous thromboembolism, active infections, renal failure, hepatic disease, neoplasms, recent trauma or surgery were excluded from the study.

Standard hematological and biochemical analyses were routinely performed at the hospital laboratory. Patients' basic clinical data and vascular risk factors, including previous antihypertensive, statin and antiplatelet treatment history are summarized in Table 1.

TABLE 1

Main clinical characteristics of the study groups

| Characteristics | n | CEA | (±SD)/n (%) | n | Control | (±SD)/n (%) | $p_{value}$ |
|---|---|---|---|---|---|---|---|
| Age (years) | 31 | 65.0 | 10.4 | 36 | 67.7 | 13.4 | 0.37 |
| Sex (% Male) | 31 | 24 | 77.4 | 36 | 21 | 58.3 | 0.08 |
| Smoking | 31 | 13 | 41.9 | 36 | 10 | 27.8 | 0.17 |
| Dyslipemia | 31 | 21 | 67.7 | 36 | 16 | 44.4 | 0.05 |
| HTN | 31 | 28 | 90.3 | 36 | 21 | 58.3 | 0.00 |
| Diabetes | 31 | 12 | 38.7 | 36 | 8 | 22.2 | 0.12 |
| Peripheral vasc. | 31 | 8 | 25.8 | 36 | 5 | 13.9 | 0.18 |
| CAD | 31 | 7 | 22.6 | 36 | 1 | 2.8 | 0.02 |
| Ischemic Stroke | 31 | 22 | 71.0 | 36 | 0 | 0.0 | 0.00 |
| Bilateral pathology > 50* | 29 | 11 | 35.5 | 36 | 6.0 | 16.7 | 0.05 |
| Fibrinogen (g/l) | 31 | 5.2 | 1.4 | 36 | 4.3 | 1.2 | 0.01 |
| Total cholesterol (mmol/l) | 31 | 4.5 | 1.4 | 36 | 3.7 | 1.2 | 0.01 |
| LDL-C (mmol/l) | 31 | 4.4 | 10.6 | 36 | 2.2 | 0.7 | 0.21 |
| HDL-C (mmol/l) | 31 | 2.1 | 4.5 | 36 | 1.2 | 0.3 | 0.28 |
| TG (mmol/l) | 31 | 1.5 | 0.7 | 36 | 1.9 | 1.0 | 0.05 |
| ESR (mm/h) | 30 | 15.7 | 10.6 | 35 | 14.7 | 10.9 | 0.71 |
| WBC × $10^6$/l | 31 | 6744 | 2483 | 30 | 7744 | 2597 | 0.11 |
| Creatinine (mg/dl) | 31 | 0.9 | 0.1 | 34 | 1.0 | 1.0 | 0.45 |
| SBP (mmHg) | 31 | 151.6 | 29.0 | 36 | 139.2 | 36.8 | 0.14 |
| Antiplatelet treatment | 29 | 26 | 83.9 | 36 | 11 | 30.6 | 0.00 |
| SBP treatment | 31 | 28 | 90.3 | 36 | 18 | 50.0 | 0.00 |
| Cholesterol treatment | 30 | 20 | 64.5 | 36 | 14 | 38.9 | 0.02 |

CAD: coronary artery disease;
ESR: erythrocyte sedimentation rate;
HDL-C: high density lipoprotein cholesterol;
HTN: hypertension;
LDL-C: low density lipoprotein cholesterol;
SBP: systolic blood pressure;
TG: triglycerides;
WBC: white blood cells.
*More than 50% contralateral stenosis on ultrasound.
Data are reported as a mean (±SD) or n (%).
Bold font: statistically significant values (p < 0.05).

Nine additional CEA patients were analyzed before and 5 years after surgical intervention.

The cardiovascular risk for both CEA and control groups was estimated according to the Systematic Coronary Risk Evaluation (SCORE) prediction model calibrated for use in Spain.

The study was approved by the local ethics committee in accordance with institutional guidelines and the Declaration of Helsinki, and the patient's or the family's written informed consent was obtained.

Sample Collection and miRNA Extraction

The serum fractions from CEA and control patients were obtained according to standard protocols. Briefly, blood samples were collected in EDTA-containing tubes just before CEA and, selectively in 9 additional patients, 5 years after CEA. Patient controls underwent blood extraction upon hospital admission. All blood samples were processed within one hour by centrifugation at 2,000 g for 10 min at 4° C., and the supernatants were quickly removed, aliquoted, and stored immediately at −80° C. For analysis, serum samples were thawed on ice and centrifuged at 3,000 g for 5 min, avoiding the presence of traces of red blood cells and other cellular debris susceptible to affect the miRNA analysis.

RNA was isolated from 200 µl of serum using the miRNeasy Mini Kit (Qiagen, Venlo, The Netherlands), according to the manufacturer's protocol, and eluted with 50 µl of nuclease-free water. Normalization of sample-to-sample variation in RNA isolation was approached including the synthetic C. elegans miRNA cel-miR-54 (Integrated DNA Technologies, Coralville, Iowa, USA) to each denatured serum sample (after the addition of QIAzol Lysis Reagent in the initial RNA extraction procedure) to avoid its degradation by endogenous serum RNases.

Real-Time RT-PCR Quantification

A fixed volume of 5 µl RNA per individual sample was reverse transcribed using the TaqMan MicroRNA RT kit (Applied BioSystems, Foster City, Calif., USA) and 2 µl of miR-638-specific stem-loop primers from the TaqMan miRNA Assay (hsa-miR-638 ID:001582 in a small-scale RT reaction [comprised of 1.10 µl of nuclease-free water, 1 µl of 10× of RT Buffer, 0.13 µl of RNase-Inhibitor (20 U/ml), 0.10 µl of 100 mM dNTPs and 0.67 µl of Multiscribe Reverse Transcriptase (50 U/ml)], using a GeneAmp 9700 PCR thermocycler system (Applied BioSystems) according to the manufacturer's instructions. To enhance sensitivity, a 2.5 µl aliquot of undiluted RT product was combined with 7.5 µl of pre-amplification solution [5 µl of TaqMan PreAmp Master Mix and 2.5 µl of 0.2×TaqMan miRNA Assay] and amplified in the GeneAmp 9700 PCR thermocycler system (Applied BioSystems) by heating to 95° C. for 10 min, followed by 10 cycles of 95° C. for 15 s, and 60° C. for 4 min.

Finally, 2.5 µl of water-diluted (1:5) pre-amplified product was combined with 5 µl of TaqMan Universal PCR Master Mix with no AmpErase UNG (Applied BioSystems), 0.5 µl of 20×TaqMan microRNA Assay, and 2 µl of nuclease-free water in a 10 µl PCR reaction. Real-time PCR was carried out on an Applied BioSystems 7900 HT thermocycler (50° C. for 2 min and 95° C. for 10 min, followed by 40 cycles of 95° C. for 15 s and 60° C. for 1 min). Data were analyzed with SDS 2.4 (Applied BioSystems). The amplification curves were individually inspected and miRNAs with abnormal amplification patterns were removed from analysis. The spiked-in cel-miR-54 (5 fmol) was measured in parallel to the miRNA-638 (cel-miR-54: ID 001361). All reactions were run in triplicate. For each sample, the relative abundance of target miRNA-638 was determined by the equation $2^{-\Delta Ct}$, in which $\Delta Ct = Ct$ miR-638 – Ct cel-miR-54, and transformed using the natural logarithm.

For the in vitro assay, $\Delta\Delta Ct$ was calculated by subtracting the $\Delta Ct$ of (TNF-α+IFN-γ)-stimulated versus non-stimulated HUVECs. The fold change in miRNA abundance was calculated with the equation $2^{-\Delta\Delta Ct}$.

Endothelial Cell Culture

Primary human umbilical vein endothelial cells (HUVECs) (Advancell, Barcelona, Spain) (4×105 cells per well in 6-well culture plates) were grown in endothelial growth medium EGM-Bullet kit (Lonza Ibérica, Spain) supplemented with 10% FCS and maintained at 37° C. in a 5% $CO_2$ atmosphere. At 70% confluence, cells were either left untreated or stimulated for 48 h with the pro-inflammatory cytokines TNF-α (100 U/ml) plus IFN-γ (1000 U/ml). Both cell pellets and supernatants were collected and immediately stored at −80° C. Total RNA extraction and real-time RT-PCR quantification of miR-638 and miR-155 in both cell pellets (10 ng RNA/sample) and cell supernatants (5 µl RNA/sample) were performed as described in the previous section using the respective TaqMan microRNA assays (hsa-miR-638: ID 001582; hsa-miR-155: ID 000479) (Applied BioSystems).

Bioinformatic Prediction of miR-638 Association with Stroke

A bioinformatic analysis was conducted to predict the target genes regulated by hsa-miR-638, using seven different publically available algorithms, including miRWALK (http://www.umm.uni-heidelberg.de/apps/zmf/mirwalk/index.html), DIANA microT v5.0 (http://diana.cslab.ece.ntua.gr/microT/), miRDB (http://mirdb.org/miRDB/), miRanda-mirSVR (http://www.microrna.org/), TargetScan 6.2 (http://www.targetscan.org/), Target¬Miner (http://www.isical.ac.in/~bioinfo_miu/targetminer20.htm) and miRTarBase (http://mirtarbase.mbc.nctu.edu.tw/index.php). Thus, the inventors obtained 3516 potential gene targets for miR-638. To reveal potential miR-638 gene targets relevant in stroke pathology, the inventors compared their gene list with the SigCS base, an integrated web-based genetic information resource for human cerebral stroke featuring 1943 non-redundant genes. Considering all etiologies from the SigCS base, 358 potential miR-638 gene targets were obtained. Narrowing the search to the "stroke" and "atherosclerosis" etiologies only (including 302 genes), the inventors found 61 genes as potential miR-638 targets. Finally, the inventors employed FatiGO (http://v4.babelomics.org/), a web tool for finding significant associations of gene ontology terms with groups of genes, to unveil potential pathways, processes and functions involving miR-638 regulation in stroke.

Statistical Analysis

Clinical-pathological parameters of CEA and control non-CEA groups were described using mean and standard deviation for continuous variables and frequencies for categorical variables, and compared using the T-test for independent samples or the Chi-square test, respectively. Normal distribution of serum miR-638 levels was assessed by quantile-quantile plot and Shapiro-Wilks test. T-test or Wilcoxon-Mann-Whitney test, depending on the normality of the distribution, was applied to assess significant differences between CEA and control groups, or within a CEA patient group at 0 and 5 years post-intervention. The relationship of miRNA-638 with vascular risk factors and treatments were analyzed by Spearman's rank correlation or by Point-Biserial correlation, where appropriate. The ability of serum miR-638 levels to discriminate between the non-CEA control group and the CEA patient group, the non-CEA control group and the CEA subgroups with different etiologies, or a CEA group at 0 and 5 years post-intervention, was assessed using Receiver Operator Characteristic (ROC) analysis. To analyze the association between high-risk atherosclerotic plaque (CEA) and serum miR-638 levels a logistic regression model was estimated. CEA/non-CEA control was used as the dependent variable and a raw and adjusted odds ratio (OR) for one unit change of miR-638 was calculated. Adjusting variables included classical vascular risk factors (HTN, CAD, fibrinogen, and cholesterol) found significantly different between CEA and non-CEA control individuals (Table 1). All tests were two-tailed and p<0.05 was considered statistically significant. Statistical analyses were conducted using R version 3.2.2 for Windows, SPSS software version 15.0 (SPSS, Chicago, Ill.) and GraphPad Prism version 6 (GraphPad Software, La Jolla, Calif.).

Results

Potential Involvement of miR-638 in Stroke

Figure 4:
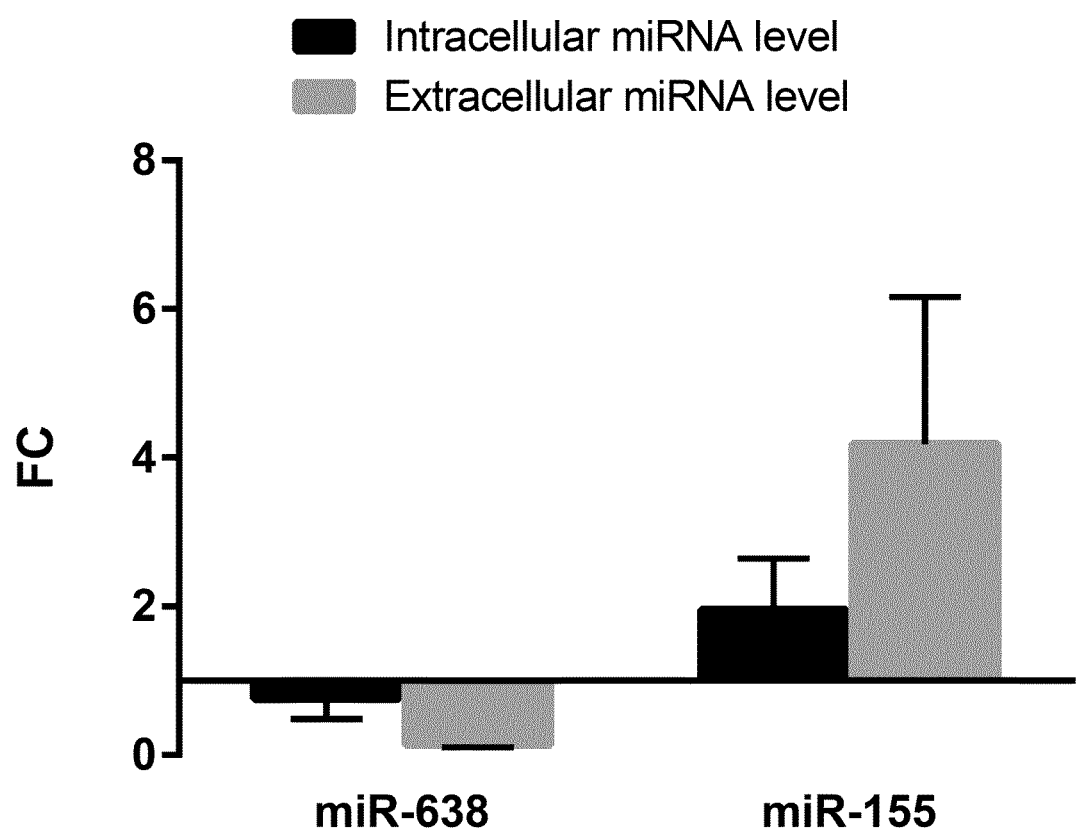
FIG. 4. Pro-inflammatory stimuli modulate the expression and release of miR-638 and miR-155 in cultured HUVECs. The relative levels of intracellular and extracellular miR-638 and miR-155 are expressed as fold change of (TNF-α+IFN-γ)-stimulated versus non-stimulated HUVECs, and are given as mean values±SD from triplicate experiments. The intracellular and extracellular levels of each miRNA are not comparable.

The major constitutive cell types participating in atherosclerotic vascular disease and contributing to atherogenesis and vulnerable plaque formation are the endothelial cells and the intimal VSMCs. miR-638, highly expressed in VSMCs, is substantially down-regulated in proliferative human VSMCs after platelet-derived growth factor (PDGF) stimulation. On the other hand, it was found that miR-638 was expressed in cultured endothelial cells. Moreover, upon pro-inflammatory stimulation, both the intracellular and released miR-638 levels were reduced compared to those found in non-stimulated cells. Conversely, pro-inflammatory cytokines up-regulated the endothelial expression and increased the release of the multi-functional miR-155, as previously described (FIG. 4).

Furthermore, 61 miR-638 potential target genes, according to different miRNA target prediction algorithms, could be related to the "stroke" and "atherosclerosis" etiologies using the SigCS base as reference. An unbiased functional enrichment analysis of this gene set using the FatiGO tool confirmed miR-638 as the only miRNA significantly represented (p<0.05), and predicted functional genes, pathways and biological processes related to stroke and significantly regulated by miR-638.

Taken together, miR-638 seems to constitute a relevant vascular miRNA participating in stroke pathophysiology and, therefore, susceptible to be tested as potential biomarker of carotid artery disease.

Characteristics of the Study Population

A total of 31 individuals undergoing CEA for high-grade stenosis, including 9 asymptomatic patients, 11 patients with a previous history of ischemic stroke, 8 patients which underwent transient ischemic attacks, and 3 patients experiencing amaurosis (CEA group), and 36 age- and sex-matched individuals visiting the neurology unit with etiologies unrelated to atherosclerotic disease, including 6 patients with a previous history of hemorrhagic stroke (control non-CEA group), were included in the study. In the whole population, CEA and non-CEA controls displayed similar characteristics except for significantly higher incidences of stroke, coronary artery disease (CAD) and hypertension, and significantly increased fibrinogen and total cholesterol values in CEA patients. Moreover, the number of patients receiving anti-platelet, cholesterol-lowering and/or blood pressure-lowering treatments was also significantly higher in the CEA group (Table 1). The symptomatic patient subgroup undergoing CEA (n=22) presented similar clinical features to the whole CEA population except for the absence of significant CAD compared to the control non-CEA group. Among the symptomatic CEA patient subgroup, those having experienced stroke (n=11) were all male and showed a significant incidence of smoking and increased levels of total cholesterol and systolic blood pressure compared to the non-CEA control. Conversely, the asymptomatic CEA patient subgroup (n=9) did not show significant differences in sex, smoking, total cholesterol and systolic blood pressure, although displayed a significant increase in the incidence of hypertension and CAD, and in fibrinogen and LDL levels compared to the control non-CEA group.

Circulating miR-638 is Decreased in CEA Patients

Figure 5:
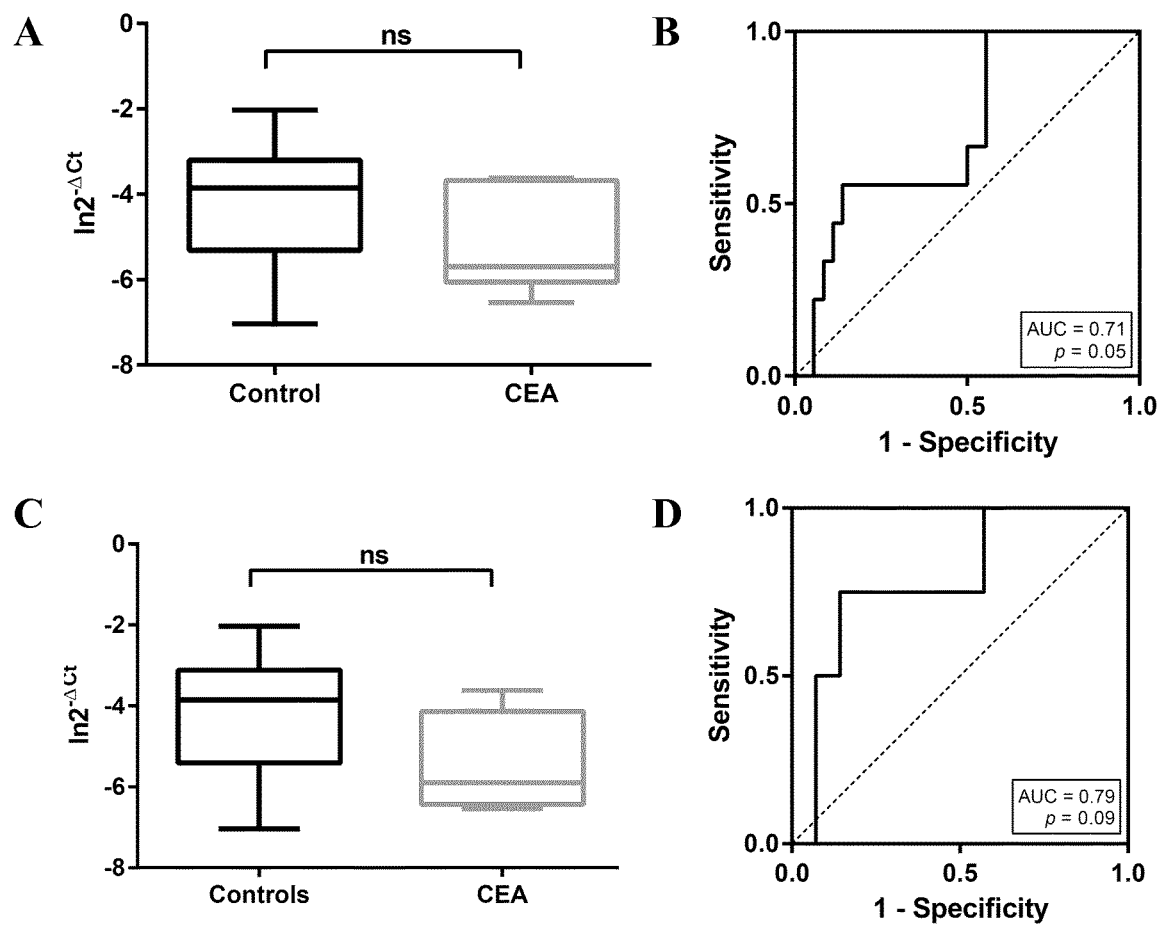
FIG. 5. Serum levels and diagnostic accuracy of miR-638 in the asymptomatic CEA patient subgroup compared to the control non-CEA group. Serum levels of miR-638 assessed by RT-qPCR are reduced in asymptomatic CEA patients (n=9) compared to control non-CEA individuals (n=36) (A), and in asymptomatic CEA patients with high cardiovascular risk (SCORE>5) (n=4) compared to control non-CEA individuals with high cardiovascular risk (n=14) (C) (* p<0.05; ns, non-significant). ln $2^{-\Delta Ct}$, miR-638 levels relative to cel-miR-54, transformed into linear form using the formula $2^{-\Delta Ct}$. All quantities have been transformed using the natural logarithm. The thick black line inside the boxes indicates the median. The top and bottom of the boxes indicate $25^{th}$ percentile and $75^{th}$ percentile. Cardiovascular risk vas determined using the SCORE chart. Receiver-operating characteristics (ROC) analysis was used to determine the diagnostic accuracy of serum miR-638 predicting CEA intervention for high-risk ischemic stroke in asymptomatic patients with: (B) low to moderate cardiovascular risk. Discrimination of CEA from non-CEA control individuals, area under the curve (AUC) 0.71 (0.53 to 0.89), and (D) high cardiovascular risk (SCORE>5). Discrimination of asymptomatic CEA+SCORE>5 patients from control non-CEA+SCORE>5 individuals, area under the curve (AUC) 0.79 (0.53 to 1.04). In all cases, the dashed lines indicate the reference line (AUC=0.5).

In the whole population of patients with carotid stenosis undergoing CEA, the relative serum level of miR-638 was significantly lower compared to individuals without atherosclerosis (non-CEA control) (p=0.007) (FIG. 1A). The ability of circulating miR-638 to differentiate the CEA group from the non-CEA control group was estimated by the ROC curve with an AUC of 0.68 (95% confidence interval (CI95%)=0.55-0.81; p=0.01) (FIG. 1B). An analogous analysis performed to the CEA symptomatic subgroup revealed that the levels of serum miR-638 were also significantly lower than those displayed by the non-CEA control group (p=0.009) (FIG. 1C), and circulating miR-638 was similarly capable to discriminate CEA symptomatic from control non-CEA individuals (AUC=0.66; CI95%=0.52-0.81; p=0.04) (FIG. 1D). Furthermore, the difference between the relative serum levels of miR-638 from the stroke patient subgroup undergoing CEA and from the non-CEA control group reached the highest statistical significance (p=0.0006) (FIG. 1E). Consequently, the discriminatory capability of circulating miR-638 between the stroke CEA patient subgroup and the non-CEA control group increased (AUC=0.76; CI95%=0.59-0.96; p=0.01) (FIG. 1F). Finally, the inventors also found reduced levels of serum miR-638 in the asymptomatic CEA subgroup respect to the non-CEA control group, although the difference was non-significant due to the reduced size of the asymptomatic CEA subgroup (n=9) (FIG. 5A). Interestingly, the serum miR-638 levels displayed a biphasic distribution among the asymptomatic CEA patients, which proved to be statistically significant (p=0.016). Moreover, the inventors found a statistically significant inverse correlation between serum miR-638 levels and asymptomatic patients having at least two of three traditional vascular risk factors: smoking, diabetes and peripheral vascular disease (rbs=−0.693; p=0.039). In addition, serum miR-638 seemed to present fairly good discriminatory power between the asymptomatic CEA subgroup and the non-CEA control group (AUC=0.71; CI95%=0.53-0.89; p=0.05) (FIG. 5B).

miR-638 was not able to differentiate the asymptomatic and symptomatic CEA subgroups (data not shown).

On the other hand, serum miR-638 was negatively correlated with the occurrence of stroke, smoker status, presence of bilateral pathology, CAD and cholesterol treatment. Conversely, serum miR-638 levels correlated positively with blood triglyceride levels, although the correlation was lost when the hemorrhagic stroke patients (n=6) were excluded from the analysis (Table 2).

TABLE 2

Correlation of serum miR-638 levels with clinical parameters and vascular risk factors in the study population Spearman's rank correlation

| Hsa-miR-638 | ρ | $p_{value}$ |
|---|---|---|
| Age (years) | 0.040 | 0.746 |
| Fibrinogen (g/l) | 0.000 | 0.998 |
| Total cholesterol (mmol/l) | 0.029 | 0.818 |
| LDL-C (mmol/l) | 0.068 | 0.583 |

TABLE 2-continued

Correlation of serum miR-638 levels with clinical parameters and vascular risk factors in the study population

| | | |
|---|---|---|
| HDL-C (mmol/l) | −0.224 | 0.068 |
| TG (mmol/l) | 0.339 | 0.005 |
| ESR (mm/h) | 0.030 | 0.812 |
| WBC × $10^6$/l | 0.058 | 0.641 |
| Creatinina | 0.024 | 0.851 |
| SBP (mg/dl) | 0.038 | 0.759 |

Biserial correlation

| Hsa-miR-638 | $r_{bs}$ | $p_{value}$ |
|---|---|---|
| Sex | 0.147 | 0.234 |
| Smoking | −0.299 | 0.014 |
| Dyslipemia | −0.156 | 0.207 |
| HTN | −0.115 | 0.352 |
| Diabetes | 0.066 | 0.595 |
| Peripheral vasc. | −0.087 | 0.484 |
| CAD | −0.242 | 0.049 |
| Ischemic Stroke | −0.292 | 0.016 |
| Bilateral pathology > 50* | −0.313 | 0.011 |
| Antiplatelet treatment | −0.205 | 0.101 |
| SBP treatment | −0.236 | 0.054 |
| Cholesterol treatment | −0.331 | 0.007 |

CAD: coronary artery disease;
ESR: erythrocyte sedimentation rate;
HDL-C: high density lipoprotein cholesterol;
HTN: hypertension;
LDL-C: low density lipoprotein cholesterol;
SBP: systolic blood pressure;
TG: triglycerides; WBC: white blood cells.
*More than 50% contralateral stenosis on ultrasound.
ρ: Spearman's correlation coefficient;
$r_{bs}$: Biserial correlation coefficient.
Bold font: statistically significant values (p < 0.05).

After logistic regression, the level of serum miR-638 was identified as independent predictor of vulnerable plaques and, therefore, of stroke risk in the CEA patient group and in the corresponding symptomatic and stroke subgroups except in the reduced size asymptomatic subgroup (Table 3).

TABLE 3

Raw and adjusted odds ratio for the association between serum miR-638 and CEA by multivariate logistic regression model.

| Variables | OR | CI 95% | $p_{value}$ | Adjusted OR* | CI 95% | $p_{value}$ |
|---|---|---|---|---|---|---|
| All patients | 0.64 | 0.45-0.89 | 0.011 | 0.62 | 0.41-0.88 | 0.013 |
| Symptomatic patients | 0.65 | 0.45-0.90 | 0.015 | 0.63 | 0.42-0.90 | 0.016 |
| Stroke patients | 0.50 | 0.29-0.77 | 0.004 | 0.44 | 0.23-0.71 | 0.003 |
| Asymptomatic patients | 0.60 | 0.32-1.07 | 0.097 | 0.61 | 0.32-1.08 | 0.102 |
| Patients with SCORE > 5 | 0.51 | 0.26-0.84 | 0.020 | 0.51 | 0.24-0.87 | 0.032 |

*CAD and Fibrinogen not used in the model due to estimation problems on standard errors.
CI, confidence interval;
OR, Odds Ratio.

Figure 2:
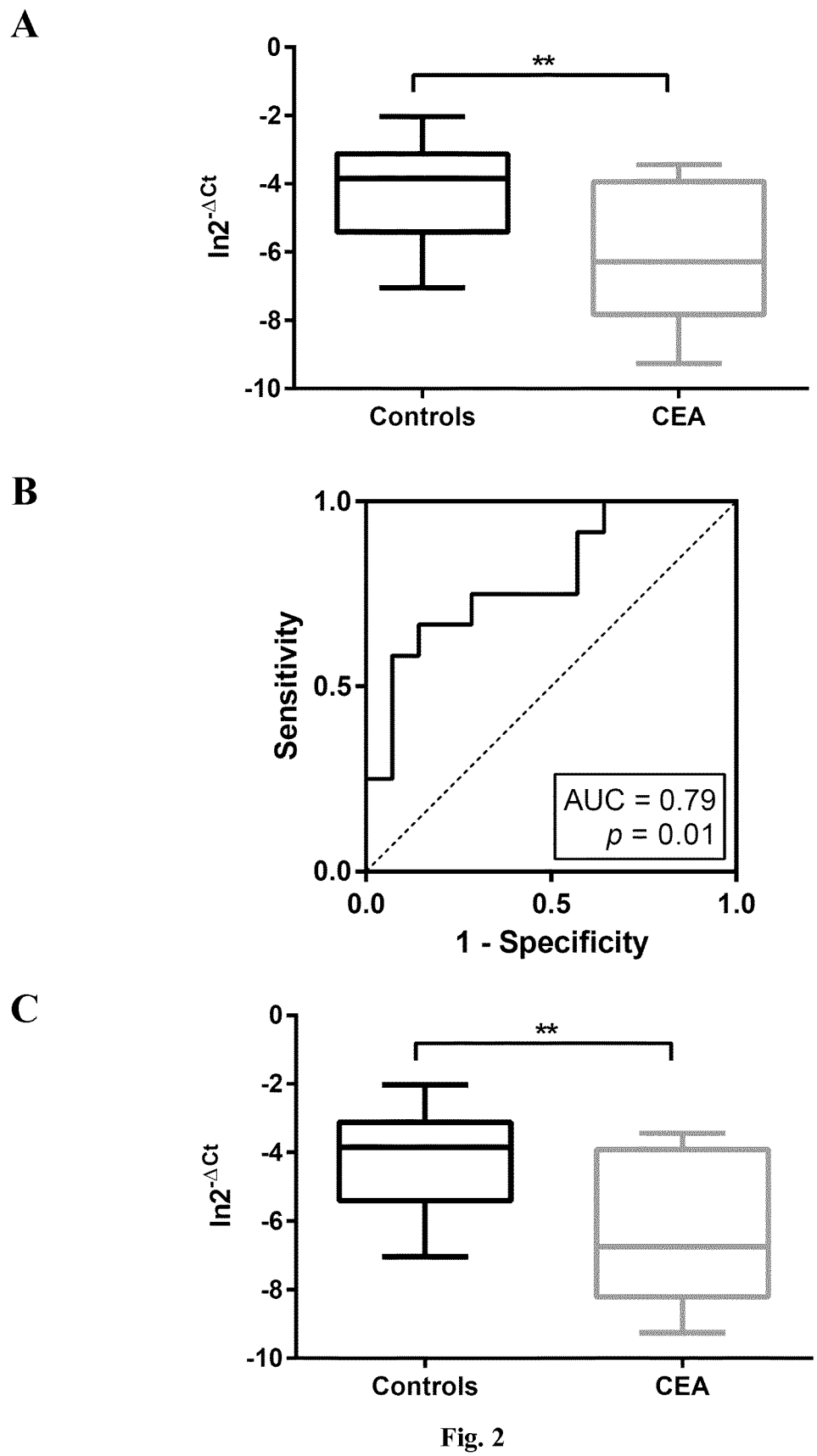
FIG. 2. Serum levels and diagnostic accuracy of miR-638 in the CEA patient group and symptomatic and stroke subgroups compared to the control non-CEA group in high cardiovascular risk individuals. Cardiovascular risk vas determined using the SCORE chart. Serum levels of miR-638 assessed by RT-qPCR are reduced in CEA patients with SCORE>5 (n=12) (A), symptomatic CEA patients with SCORE>5 (n=8) (C), and stroke CEA patients with SCORE>5 (n=7) (E), compared to control non-CEA individuals with SCORE>5 (n=14) (** p<0.01). ln $2^{-\Delta Ct}$, miR-638 levels relative to cel-miR-54, transformed into linear form using the formula $2^{-\Delta Ct}$. All quantities have been transformed using the natural logarithm. The thick black line inside the boxes indicates the median. The top and bottom of the boxes indicate $25^{th}$ percentile and $75^{th}$ percentile. Receiver-operating characteristics (ROC) analysis was used to determine the diagnostic accuracy of serum miR-638 predicting CEA intervention for high-risk ischemic stroke in high cardiovascular risk individuals (SCORE>5) with the highest sensitivity and specificity. (B) Discrimination of CEA from non-CEA control individuals, area under the curve (AUC) 0.79 (0.61 to 0.97). (D) Discrimination of symptomatic CEA patients from control non-CEA individuals, AUC 0.79 (0.59 to 1.00). (F) Discrimination of stroke CEA patients from control non-CEA individuals AUC 0.85 (0.66 to 1.04). In all cases, the dashed lines indicate the reference line (AUC=0.5).
Figure 2:
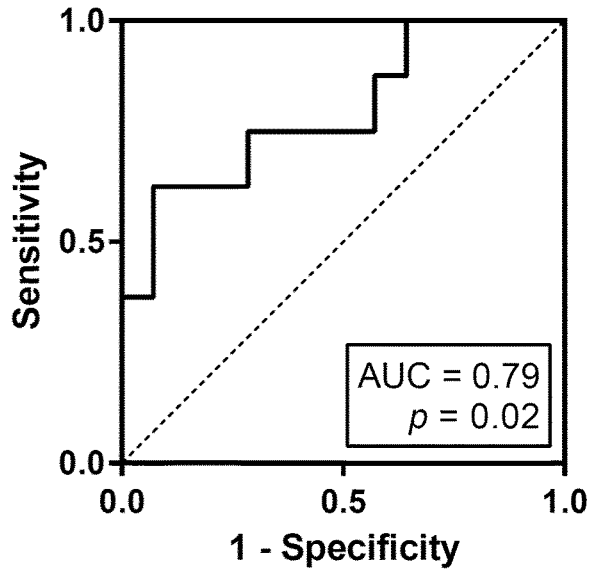
Figure 2:
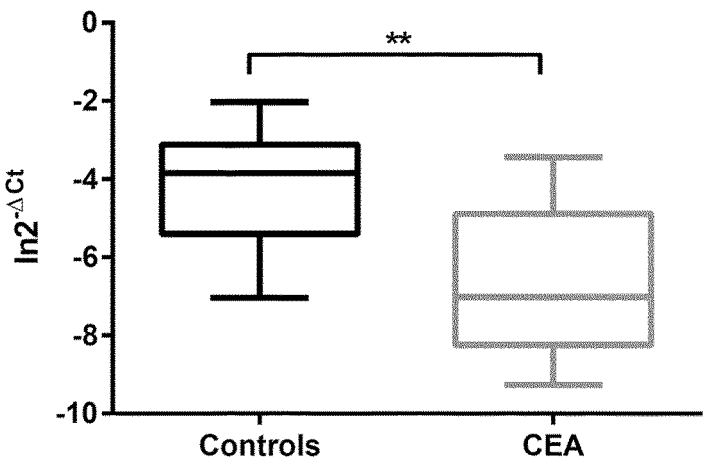
Figure 2:
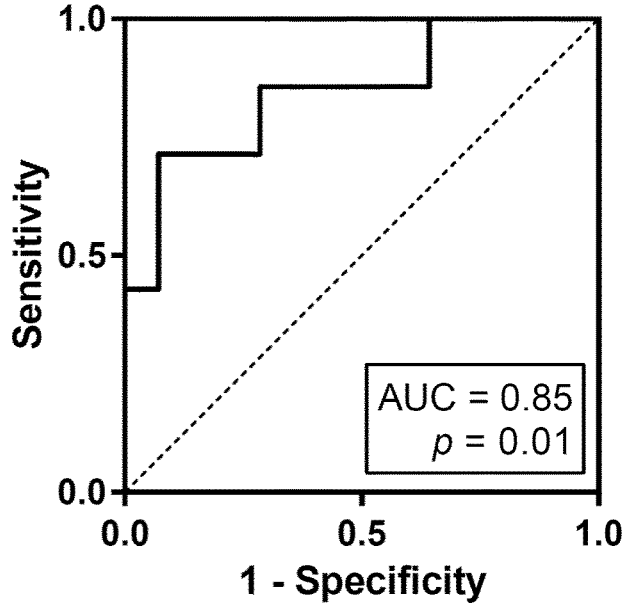

Systematic Coronary Risk Evaluation (SCORE) Increases the Accuracy of Circulating miR-638 for Vulnerable Carotid Plaque Prediction in High Cardiovascular Risk Individuals Since CAD was significantly correlated with decreased serum miR-638 levels, it was further evaluated whether focusing the analysis of serum miR-638 to high cardiovascular risk individuals using the SCORE prediction model (SCORE>5; n=12 from the CEA group, and n=14 from the non-CEA control group) would improve its diagnostic accuracy. An increased incidence of stroke in CEA patients was the unique clinical parameter significantly different between CEA and non-CEA control high cardiovascular risk subgroups. The inventors confirmed that the serum levels of miR-638 were significantly lower in the CEA+SCORE>5 subgroup (n=12) (FIG. 2A), the symptomatic CEA+SCORE>5 subgroup (n=8) (FIG. 2C), and the stroke CEA+SCORE>5 subgroup (n=7) (FIG. 2E), compared to the non-CEA control+SCORE>5 subgroup (n=14) (p=0.008, p=0.009, and p=0.003, respectively). Again the difference in serum miR-638 levels between the asymptomatic CEA+SCORE>5 subgroup (n=4) and the non-CEA control+SCORE>5 subgroup was not significant, likely due to the reduced size of the asymptomatic CEA+SCORE>5 subgroup (FIG. 5C). Inventors also stratified the ROC analysis of serum miR-638 levels to assess the sensitivity and specificity of vulnerable plaque and stroke risk prediction among the above-described subgroups with SCORE>5 and obtained an improved diagnostic accuracy (CEA+SCORE>5 subgroup vs. non-CEA control+SCORE>5 subgroup: AUC=0.79; CI95%=0.61-0.97; p=0.01 (FIG. 2B); symptomatic CEA+SCORE>5 subgroup vs. non-CEA control+SCORE>5 subgroup: AUC=0.79; CI95%=0.59-1.00; p=0.02 (FIG. 2D); stroke CEA+SCORE>5 subgroup vs. non-CEA control+SCORE>5 subgroup: AUC=0.85; CI95%=0.66-1.04; p=0.01 (FIG. 2F); asymptomatic CEA+SCORE>5 subgroup vs. non-CEA control+SCORE>5 subgroup: AUC=0.79; CI95%=0.53-1.04; p=0.09) (FIG. 5D).

Multivariate logistic regression analysis demonstrated that serum miR-638 levels were also able to independently predict carotid plaque instability in high cardiovascular risk individuals (adjusted OR: 0.51, 95% CI: 0.24-0.87; p=0.032) (Table 3).

Thus, circulating miR-638 might become a useful biomarker for vulnerable atherosclerotic carotid plaques and ischemic stroke prediction in high cardiovascular risk individuals.

Prognostic Value of Circulating miR-638 in Long-Term Follow-Up CEA Patients

Figure 3:
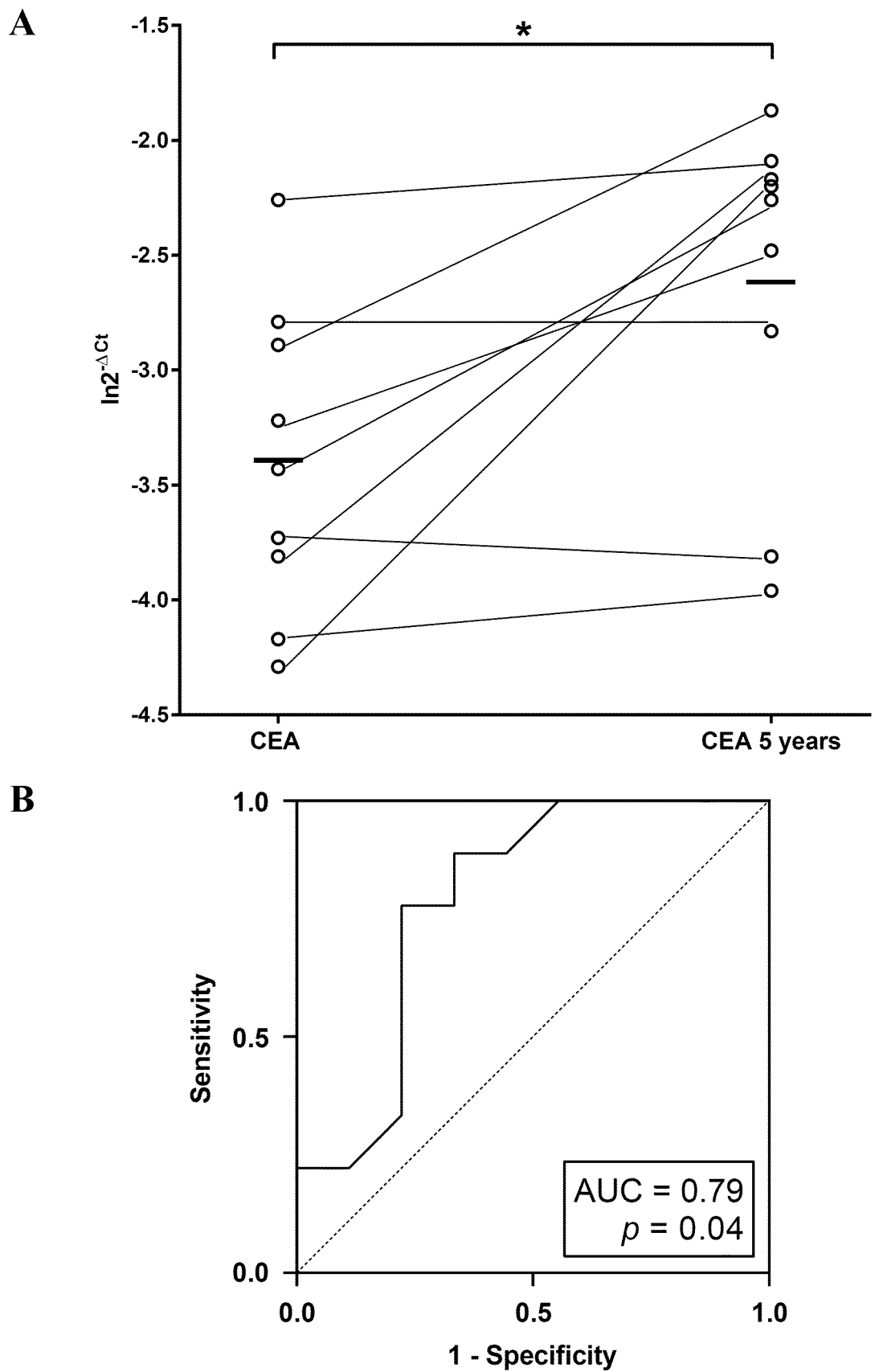
FIG. 3. Prognostic accuracy of circulating miR-638 in long-term follow-up CEA patients. (A) Comparison of serum miR-638 levels between 0 and 5 years post-intervention in CEA patients (n=9) (* p<0.05). (B) ROC curve analysis to assess the discrimination potential of serum miR-638 levels for CEA before and at 5 years after revascularization, AUC 0.79 (0.57 to 1.01).

It was further assessed whether serum miR-638 would be able to predict the outcome of aggressive medical therapy (CEA plus pharmacological treatment with risk factor modification) on atherosclerotic disease progression in the long term. The inventors analyzed serum miR-638 levels form 9 CEA patients just before intervention and after a 5-year follow-up. Smoking status probed the only significantly different risk factor among both time frames (Table 4) because medical management of CEA patients advises smoking cessation. The mean serum levels of miR-638 was found significantly increased at 5 years after CEA intervention (p=0.04) (FIG. 3A). Moreover, circulating miR-638 attained good discrimination for atherosclerotic carotid stenosis in CEA patients before and after long-term follow up post-intervention (AUC=0.79, CI95%=0.57-1.01; p=0.04) (FIG. 3B). Thus, circulating miR-638 levels might have prognostic value for atherosclerotic disease progression in CEA-intervened patients and, consequently, for secondary stroke prevention.

TABLE 4

Main clinical characteristics of CEA patients at 0 and 5 years post-intervention

| Characteristics | n | CEA | (±SD)/n (%) | n | post CEA (5 years) | (±SD)/n (%) | $p_{value}$ |
|---|---|---|---|---|---|---|---|
| Age (years) | 9 | 64 | 8.0 | 9 | 69 | 8.0 | — |
| Sex (% Male) | 9 | 9 | 100.0 | 9 | 9 | 100.0 | — |
| Smoking | 9 | 4 | 44.4 | 9 | 0 | 0.0 | 0.04 |
| Dyslipidemia | 9 | 4 | 44.4 | 9 | 5 | 55.6 | 0.50 |
| HTN | 9 | 8 | 88.9 | 9 | 8 | 88.9 | 0.77 |
| Peripheral vasc. | 9 | 7 | 77.8 | 9 | 7 | 77.8 | 0.71 |
| CAD | 9 | 1 | 11.1 | 9 | 2 | 22.2 | 0.50 |
| Total cholesterol (mmol/l) | 9 | 5.2 | 0.7 | 9 | 4.7 | 1.1 | 0.26 |
| LDL-C (mmol/l) | 9 | 3.4 | 0.7 | 9 | 2.6 | 1.0 | 0.07 |
| HDL-C (mmol/l) | 9 | 1.1 | 0.2 | 9 | 1.3 | 0.3 | 0.12 |
| TG (mmol/l) | 9 | 1.5 | 0.5 | 9 | 1.8 | 1.3 | 0.46 |
| WBC × $10^6$/l | 9 | 6679 | 1267 | 9 | 7460 | 2285 | 0.38 |
| Antiplatelet treatment | 9 | 8 | 88.9 | 9 | 7 | 77.8 | 0.50 |
| Cholesterol treatment | 9 | 3 | 33.3 | 9 | 6 | 66.7 | 0.17 |

CAD: coronary artery disease;
HDL-C: high density lipoprotein cholesterol;
HTN: hypertension;
LDL-C: low density lipoprotein cholesterol;
TG: triglycerides;
WBC: white blood cells.
Data are reported as a mean (±SD) or n (%).
Bold font: statistically significant values (p < 0.05).

The invention claimed is:

1. A method for treating unstable atherosclerotic plaque or stroke in a subject that comprises:
   (i) determining the expression level of circulating miRNA miR-638 in a sample from a subject suspected of having unstable atherosclerotic plaque or suffering from a stroke;
   (ii) comparing the expression level obtained in (i) to a reference value;
   (iii) selecting subjects having unstable atherosclerotic plaque or having high probability of suffering from a stroke as those wherein the expression level of circulating miR-638 in (i) is decreased with respect to the reference value and;
   (iv) administering a therapy comprising a revascularization procedure or a pharmacological treatment to the subjects selected in (iii).

2. The method according to claim 1, wherein the revascularization procedure is carotid endarterectomy (CEA) or carotid artery stenting (CAS).

3. The method according to claim 1, wherein the pharmacological treatment is selected from an anti-platelet treatment, a cholesterol-reducing treatment, a blood pressure-lowering treatment, and a smoking cessation therapy.

4. The method according to claim 1, wherein the subject has already suffered from a cerebrovascular event previously.

5. The method according to claim 4, wherein the cerebrovascular event is selected from the group consisting of transient ischemic attack (TIA), stroke, or amaurosis fugax.

6. The method according to claim 1, wherein if the subject has not suffered from a cerebrovascular event, then a vascular disease risk factor selected from the group consisting of smoking, hyperlipidemia, high blood pressure, diabetes and peripheral vascular disease or a combination thereof is additionally determined.

7. The method according to claim 6, wherein if the subject shows at least two vascular disease risk factors, then a therapy comprising a revascularization procedure and/or pharmacological therapy is selected.

8. The method according to claim 1, wherein the systematic coronary risk evaluation (SCORE) is additionally determined, and wherein if SCORE is equal to or higher than 5, then a therapy comprising a revascularization procedure and/or pharmacological therapy is selected.

9. The method according to claim 1, wherein the carotid stenosis grade is additionally determined, and wherein if the subject suffers from high grade carotid stenosis, then a therapy comprising a revascularization procedure and/or pharmacological therapy is selected.

10. The method according to claim 1, wherein the reference value is a miRNA miR-638 expression level determined in a sample from a control subject whose degree of carotid stenosis is equal to or lower than 30%.

11. The method according to claim 10, wherein the control subject has not suffered from ischemic stroke, from atherosclerosis, particularly from carotid atherosclerosis, or from carotid artery disease.

12. The method according to claim 10, wherein the control subject shows a SCORE equal to or higher than 5.

\* \* \* \* \*